US012746401B2

(12) United States Patent
Meskens

(10) Patent No.: US 12,746,401 B2
(45) Date of Patent: Sep. 29, 2026

(54) QUANTIZED WAVEFORM POWER TRANSMISSION

(71) Applicant: Cochlear Limited, Macquarie University (AU)

(72) Inventor: Werner Meskens, Opwijk (BE)

(73) Assignee: Cochlear Limited, Macquarie University (AU)

( * ) Notice: Subject to any disclaimer, the term of this patent is extended or adjusted under 35 U.S.C. 154(b) by 187 days.

(21) Appl. No.: 18/247,710

(22) PCT Filed: Sep. 2, 2021

(86) PCT No.: PCT/IB2021/058017
§ 371 (c)(1),
(2) Date: Apr. 3, 2023

(87) PCT Pub. No.: WO2022/074479
PCT Pub. Date: Apr. 14, 2022

(65) Prior Publication Data
US 2023/0405347 A1 Dec. 21, 2023

Related U.S. Application Data

(60) Provisional application No. 63/089,698, filed on Oct. 9, 2020.

(51) Int. Cl.
*A61N 1/378* (2006.01)
*H02J 50/12* (2016.01)
(Continued)

(52) U.S. Cl.
CPC ............ *A61N 1/3787* (2013.01); *H02J 50/12* (2016.02); *H02J 50/20* (2016.02); *H02J 50/80* (2016.02); *A61N 1/37223* (2013.01)

(58) Field of Classification Search
CPC ............. H02J 50/12; H02J 50/80; H02J 50/20
See application file for complete search history.

(56) References Cited

U.S. PATENT DOCUMENTS 9,132,276 B2 9/2015 Meskens
11,769,949 B2 * 9/2023 Zolomy .................. H01Q 1/50 343/702
(Continued)

FOREIGN PATENT DOCUMENTS

CN 103378658 A 10/2013
CN 204947740 U 1/2016
(Continued)

OTHER PUBLICATIONS

International Search Report and Written Opinion in counterpart International Application No. PCT/IB2021/058017, mailed Dec. 7, 2021, 9 pages.
(Continued)

*Primary Examiner* — Rexford N Barnie
*Assistant Examiner* — Esayas G Yeshaw
(74) *Attorney, Agent, or Firm* — Edell, Shapiro & Finnan, LLC

(57) ABSTRACT

Presented herein are techniques for wirelessly transferring power signals (power) through the use of a quantized wave-shaped signal, referred to herein as “quantized waveform.” In particular, a quantized waveform generator comprises a pulse generator and a set of amplifiers that are grouped over a distributed resonance capacitor part of a series resonant tank circuit. These amplifiers are driven in a predefined sequence of pulses in order to generate a step function output (quantized waveform). The quantized waveform is used to drive a power transmission coil to cause the power transmission coil to emit wireless power signals at a predetermined operating frequency. The predefined sequence used to drive the amplifiers is such that one or
(Continued)

more harmonic components of the operating frequency are substantially eliminated.

22 Claims, 27 Drawing Sheets

(51) Int. Cl.

| | |
|---|---|
| ***H02J 50/20*** | (2016.01) |
| ***H02J 50/80*** | (2016.01) |
| *A61N 1/372* | (2006.01) |

(56) References Cited

U.S. PATENT DOCUMENTS

| | | | | |
|---|---|---|---|---|
| 2010/0184371 | A1 | 7/2010 | Cook et al. | |
| 2012/0242284 | A1 | 9/2012 | Wheatly, III et al. | |
| 2013/0181664 | A1* | 7/2013 | Min | H04B 5/79 320/108 |
| 2013/0278071 | A1 | 10/2013 | Komiyama | |
| 2014/0039299 | A1* | 2/2014 | Foo | A61B 5/055 600/417 |
| 2015/0069854 | A1 | 3/2015 | Kim et al. | |
| 2017/0093341 | A1* | 3/2017 | Poulin | H03F 3/189 |
| 2018/0076999 | A1* | 3/2018 | Luo | H03F 3/191 |
| 2018/0138747 | A1* | 5/2018 | Mao | H02J 50/12 |
| 2019/0140352 | A1 | 5/2019 | Zolomy et al. | |
| 2019/0167989 | A1* | 6/2019 | Guyon | A61N 1/3787 |
| 2021/0013848 | A1* | 1/2021 | Waldmeier | H03F 3/2173 |
| 2022/0224385 | A1* | 7/2022 | Kotilainen | H01Q 3/24 |
| 2023/0405347 | A1* | 12/2023 | Meskens | H01F 38/14 |

FOREIGN PATENT DOCUMENTS

| | | | |
|---|---|---|---|
| EP | 3096437 | A1 | 11/2016 |
| JP | H11224822 | A | 8/1999 |
| WO | 2017-131345 | A1 | 8/2017 |
| WO | 2017187610 | A1 | 11/2017 |

OTHER PUBLICATIONS

T. Volk et al., "Wireless Power Distribution System for Brain Implants", Conference Paper in Conference Record—IEEE Instrumentation and Measurement Technology Conference, May 2015, DOI: 10.1109/12MTC.2015.7151452, https://www.researchgate.net/profile/C_Alexis_Gkogkidis/publication/280084142_Wireless_power_distribution_system_for_brain_implants/links/55a767cd08ae51639c577e2d/Wireless-power-distribution-system-for-brain-implants.pdf?origin=publication_detail, 7 pages.

Jason Avron Samuels, "Design and Implementation of an off-grid PV drive system for small-scale fresh produce cooling", Thesis, Nov. 2017, https://www.researchgate.net/figure/A-current-summation-of-the-resonant-capacitor-currents-making-up-the-secondary-winding_fig13_321905669, 158 pages.

Sze Sing Lee, "Single-Stage Switched-Capacitor Module (S3CM) Topology for Cascaded Multilevel Inverter", IEEE Transactions on Power Electronics, vol. 33, No. 10, Oct. 2018, 4 pages.

Maxim Integrated Products, "Class D Amplifiers: Fundamentals of Operation and Recent Developments", Jan. 31, 2007, 12 pages.

DonH56, "Class D Amplifiers 101", Apr. 19, 2019, https://www.audiosciencereview.com/forum/index.php?threads/ class-d-amplifiers-101.7355/, 18 pages.

NXP, "Booster Circuit Study Report", Rev. 0.5—Aug. 17, 2011, PLR-IP1004-0014, 19 pages.

Extended European Search Report in counterpart European Application No. 21877079.0-1002, mailed Nov. 21, 2024, 29 pages.

* cited by examiner

| BRIDGES | APPLIED 2-STEP PULSE SEQUENCE | 3-STEP PULSE SEQUENCE | QUANTIZED WAVEFORM |
|---|---|---|---|
| 362(1), 362(2), 362(3), 362(4) | a, e, 0, 0 | A1 |  |
| 362(5), 362(6), 362(7), 362(8) | h, d, 0, 0 | B2 | |
| 362(1), 362(2), 362(3), 362(4) | a, e, a, e | A1, A1 |  |
| 362(5), 362(6), 362(7), 362(8) | h, d, h, d | B2, B2 | |
| 362(1), 362(2), 362(3), 362(4) | a, c, e, f | A1, A2 |  |
| 362(5), 362(6), 362(7), 362(8) | g, h, b, d | B1, B2 | |

QUANTIZED WAVEFORM POWER TRANSMISSION

BACKGROUND

Field of the Invention

The present invention relates generally to power transmission with quantized waveforms.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a wireless power transmitter unit is provided. The wireless power transmitter unit comprises: a resonant tank circuit; and a quantized waveform generator having an output coupled to the resonant tank circuit, wherein the quantized waveform generator is configured to generate a predetermined quantized waveform that, when delivered to the resonant tank circuit, causes emission of wireless power signals having a selected harmonic emission spectrum in which one or more predetermined harmonic emissions are substantially eliminated.

In another aspect, a wireless power transmitter unit is provided. The wireless power transmitter unit comprises: a transmit coil; a plurality of capacitors each connected in series with the transmit coil to form a resonant tank circuit; a plurality of amplifiers; and a pulse generator configured to independently drive each of the plurality of amplifiers with a plurality of pulse sequences that generate a quantized waveform at the transmit coil that induces an inductive power transmission from which one or more harmonic emissions are absent.

In another aspect, an apparatus is provided. The apparatus comprises: a plurality of signal sources; a plurality of amplifiers configured to be selectively driven by the plurality of signal sources; a transmit coil; and at least one array of capacitors connected between the plurality of amplifiers and the transmit coil, wherein the transmit coil emits a wave-shaped power signal that is derived from a combination of at least two outputs from the plurality of amplifiers.

In another aspect, a method is provided. The method comprises: selectively activating a predefined pulse sequence to generate a quantized waveform; and driving a transmit coil with the quantized waveform to emit wireless power signals at a predetermined operating frequency.

In another aspect a wireless power transmitter is provided. The wireless power transmitter comprises: a transmit coil; and a set of amplifiers connected to the transmit coil via a capacitor array in series with the transmit coil to form a resonant tank circuit, wherein the amplifiers are driven in a predefined sequence resulting in a step function approximating at least one of biphasic wave shape or a sinusoidal wave shape.

In another aspect a wireless power transmitter is provided. The wireless power transmitter comprises: a resonant tank circuit comprising a radio-frequency (RF) coil and a plurality of distributed capacitors each connected in series with the RF coil; a quantized waveform generator having an output coupled to the resonant tank circuit, wherein the quantized waveform generator comprises a plurality of amplifiers and a pulse generator comprises at least two voltage sources configured to independently drive each of the plurality of amplifiers with a plurality of pulse sequences that collectively generate a quantized waveform at the output of the plurality of amplifiers, wherein the quantized waveform generator is configured to generate a predetermined quantized waveform that, when delivered to the resonant tank circuit, causes emission of wireless power signals having a selected harmonic emission spectrum in which one or more predetermined harmonic emissions are substantially eliminated; and a data modulator configured to modulate the wireless power signals with data.

BRIEF DESCRIPTION OF THE DRAWINGS

Embodiments of the present invention are described herein in conjunction with the accompanying drawings, in which.

DETAILED DESCRIPTION

Presented herein are techniques for wirelessly transferring power signals (power) through the use of a quantized wave-shaped signal, sometimes referred to herein as "quantized waveform." In particular, a quantized waveform generator comprises a pulse generator and a set of amplifiers (e.g., efficient Class-D amplifiers) that are grouped over a distributed resonance capacitor part of a series resonant tank circuit. These amplifiers are driven in a predefined sequence in order to generate a step function output (quantized waveform). The quantized waveform is used to drive a power transmission coil to cause the power transmission coil to emit wireless power signals at a predetermined operating frequency. The predefined sequence used to drive the amplifiers is such that one or more harmonic components of the operating frequency are substantially eliminated.

Merely for ease of description, the techniques presented herein are primarily described with reference to a specific implantable medical device system, namely a cochlear implant system. However, it is to be appreciated that the techniques presented herein may also be implemented by other types of implantable medical devices, implantable medical device systems, and/or other types of devices/systems utilizing inductive/wireless power transfer/transmission. For example, the techniques presented herein may be implemented by other auditory prosthesis systems that include one or more other types of auditory prostheses, such as middle ear auditory prostheses, bone conduction devices, direct acoustic stimulators, electro-acoustic prostheses, auditory brain stimulators, etc. The techniques presented herein may also be used with tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc. The techniques presented herein may also or alternatively be used to transfer power from different inductive power transmitting devices (e.g., an inductive transfer primary) to inductive power receiving devices (e.g., an inductive transfer secondary), such as in the context of wearable or portable electronic devices, Radio-frequency identification (RFID) tags, consumer electronic devices, appliances, etc.

Figure 1A:
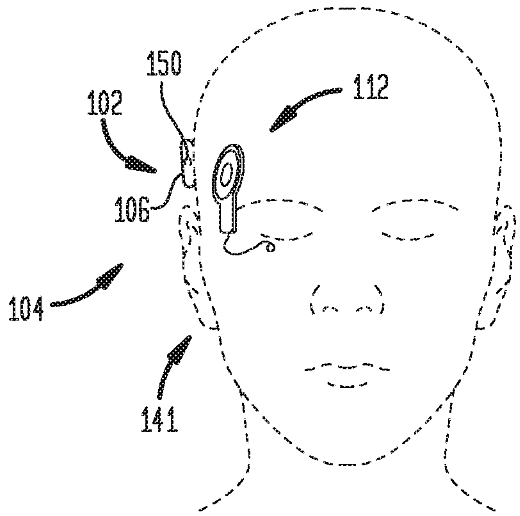
FIG. 1A illustrates a cochlear implant system, in accordance with certain embodiments presented herein.
Figure 1B:
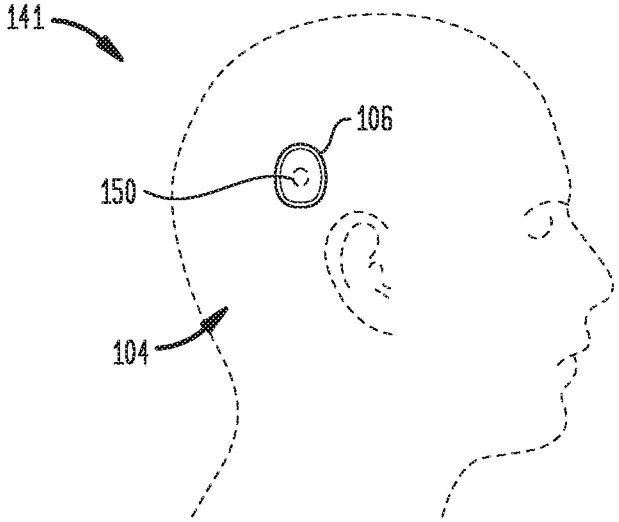
FIG. 1B is a side view of a recipient wearing a sound processing unit of the cochlear implant system of FIG. 1A.
Figure 1C:
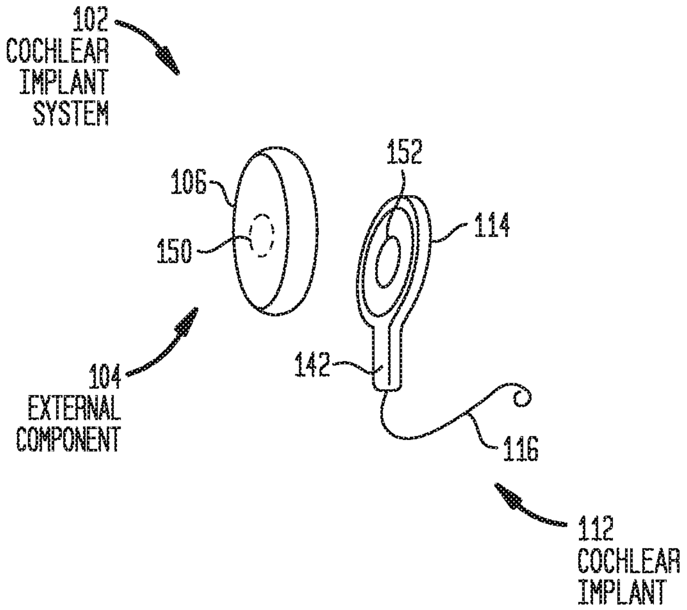
FIG. 1C is a schematic view of components of the cochlear implant system of FIG. 1A.
Figure 1D:
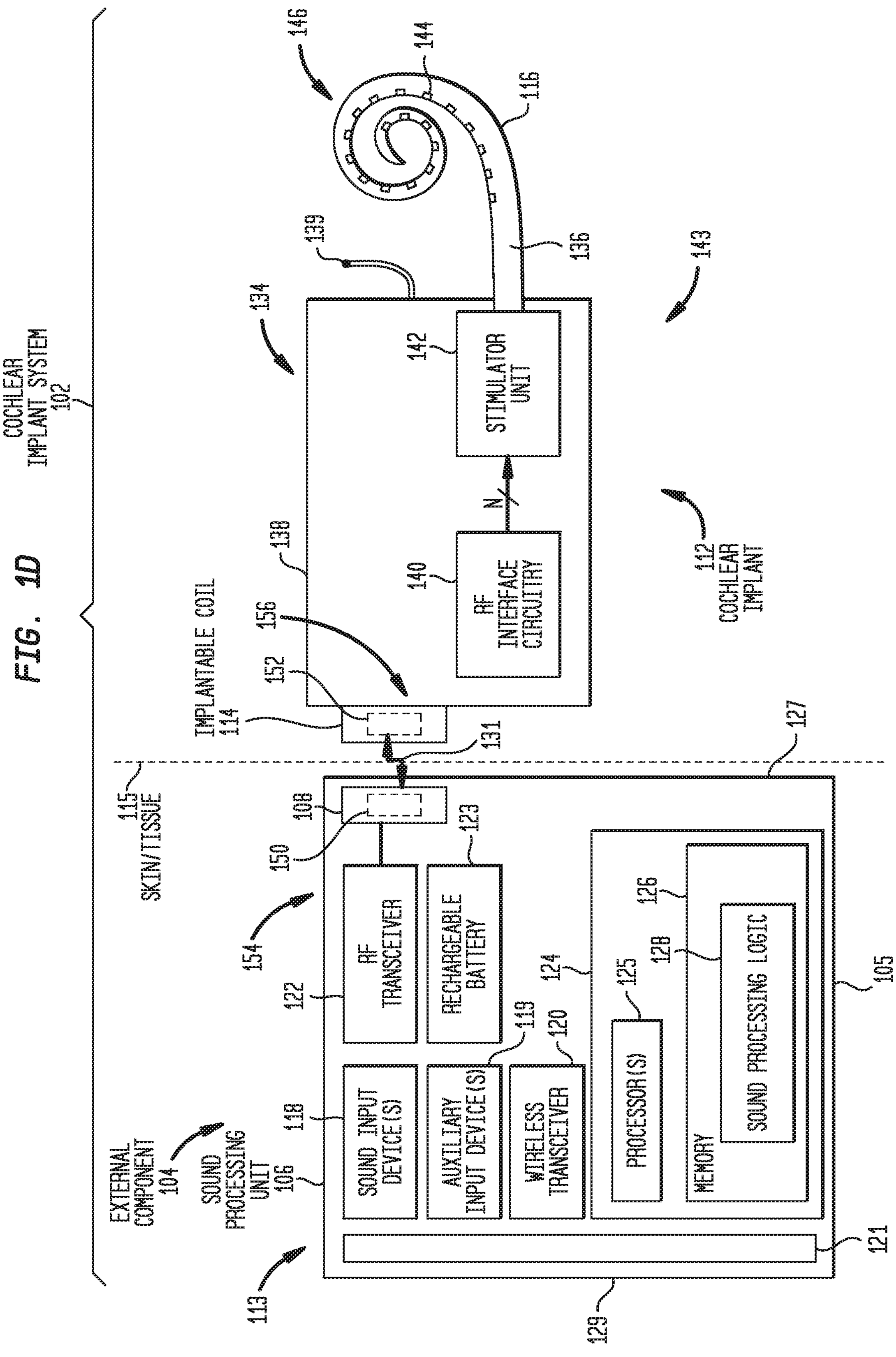
FIG. 1D is a block diagram of the cochlear implant system of FIG. 1A.

FIGS. 1A-1D illustrates an example cochlear implant system 102 configured to implement certain embodiments of the techniques presented herein. The cochlear implant system 102 comprises an external component 104 and an implantable component 112. In the examples of FIGS. 1A-1D, the implantable component is sometimes referred to as a "cochlear implant." FIG. 1A illustrates the cochlear implant 112 implanted in the head 141 of a recipient, while FIG. 1B is a schematic drawing of the external component 104 worn on the head 141 of the recipient. FIG. 1C is another schematic view of the cochlear implant system 102, while FIG. 1D illustrates further details of the cochlear implant system 102. For ease of description, FIGS. 1A-1D will generally be described together.

As noted, cochlear implant system 102 includes an external component 104 that is configured to be directly or indirectly attached to the body of the recipient and an implantable component 112 configured to be implanted in the recipient. In the examples of FIGS. 1A-1D, the external component 104 comprises a sound processing unit 106, while the cochlear implant 112 includes an internal coil 114, a stimulator unit 142, and an elongate stimulating assembly 116 configured to be implanted in the recipient's cochlea.

In the example of FIGS. 1A-1D, the sound processing unit 106 is an off-the-ear (OTE) sound processing unit, sometimes referred to herein as an OTE component, that is configured to send data and power to the implantable component 112. In general, an OTE sound processing unit is a component having a generally cylindrically shaped housing 105 and which is configured to be magnetically coupled to the recipient's head (e.g., includes an integrated external magnet 150 configured to be magnetically coupled to an implantable magnet 152 in the implantable component 112). The OTE sound processing unit 106 also includes an integrated external (headpiece) coil 108 that is configured to be inductively coupled to the implantable coil 114.

It is to be appreciated that the OTE sound processing unit 106 is merely illustrative of the external devices that could operate with implantable component 112. For example, in alternative examples, the external component may comprise a behind-the-ear (BTE) sound processing unit or a micro-BTE sound processing unit and a separate external. In general, a BTE sound processing unit comprises a housing that is shaped to be worn on the outer ear of the recipient and is connected to the separate external coil assembly via a cable, where the external coil assembly is configured to be magnetically and inductively coupled to the implantable coil 114. It is also to be appreciated that alternative external components could be located in the recipient's ear canal, worn on the body, etc.

FIGS. 1A-1D illustrate an arrangement in which the cochlear implant system 102 includes an external component. However, it is to be appreciated that embodiments of the present invention may be implemented in cochlear implant systems having alternative arrangements. For example, embodiments presented herein can be implemented by a totally implantable cochlear implant or other totally implantable medical device. A totally implantable medical device is a device in which all components of the device are configured to be implanted under skin/tissue of a recipient. Because all components are implantable, a totally implantable medical device operates, for at least a finite period of time, without the need of an external device/component. However, an external component can be used to, for example, charge the internal power source (battery) of the totally implantable medical device.

Returning to the specific example of FIGS. 1A-1D, FIG. 1D illustrates that the OTE sound processing unit 106 comprises one or more input devices 113 that are configured to receive input signals (e.g., sound or data signals). The one or more input devices 113 include one or more sound input devices 118 (e.g., microphones, audio input ports, telecoils, etc.), one or more auxiliary input devices 119 (e.g., audio ports, such as a Direct Audio Input (DAI), data ports, such as a Universal Serial Bus (USB) port, cable port, etc.), and a wireless transmitter/receiver (transceiver) 120. However, it is to be appreciated that one or more input devices 113 may include additional types of input devices and/or less input devices (e.g., the wireless short range radio transceiver 120 and/or one or more auxiliary input devices 119 could be omitted).

The OTE sound processing unit 106 also comprises the external coil 108, a charging coil 121, a closely-coupled transmitter/receiver (RF transceiver) 122, sometimes referred to as or radio-frequency (RF) transceiver 122, at least one rechargeable battery 123, and a processing module 124. The processing module 124 comprises one or more processors 125 and a memory device (memory) 126 that includes sound processing logic 128. The memory device 126 may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors 125 are, for example, microprocessors or microcontrollers that execute instructions for the sound processing logic 128 stored in memory device 126.

The implantable component 112 comprises an implant body (main module) 134, a lead region 136, and the intra-cochlear stimulating assembly 116, all configured to be implanted under the skin/tissue (tissue) 115 of the recipient. The implant body 134 generally comprises a hermetically-sealed housing 138 in which RF interface circuitry 140 and a stimulator unit 142 are disposed. The implant body 134 also includes the internal/implantable coil 114 that is generally external to the housing 138, but which is connected to the transceiver 140 via a hermetic feedthrough (not shown in FIG. 1D).

As noted, stimulating assembly 116 is configured to be at least partially implanted in the recipient's cochlea. Stimulating assembly 116 includes a plurality of longitudinally spaced intra-cochlear electrical stimulating contacts (electrodes) 144 that collectively form a contact or electrode array 146 for delivery of electrical stimulation (current) to the recipient's cochlea.

Stimulating assembly 116 extends through an opening in the recipient's cochlea (e.g., cochleostomy, the round window, etc.) and has a proximal end connected to stimulator unit 142 via lead region 136 and a hermetic feedthrough (not shown in FIG. 1D). Lead region 136 includes a plurality of conductors (wires) that electrically couple the electrodes 144 to the stimulator unit 142. The implantable component 112 also includes an electrode outside of the cochlea, sometimes referred to as the extra-cochlear electrode (ECE) 139.

As noted, the cochlear implant system 102 includes the external coil 108 and the implantable coil 114. The external magnet 152 is fixed relative to the external coil 108 and the implantable magnet 152 is fixed relative to the implantable coil 114. The magnets fixed relative to the external coil 108 and the implantable coil 114 facilitate the operational alignment of the external coil 108 with the implantable coil 114. This operational alignment of the coils enables the external component 104 to transmit data and power to the implantable component 112 via a closely-coupled wireless RF link 131 formed between the external coil 108 with the implantable coil 114. In certain examples, the closely-coupled wireless link 131 is a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, sound processing unit 106 includes the processing module 124. The processing module 124 is configured to convert received input signals (received at one or more of the input devices 113) into output signals for use in stimulating a first ear of a recipient (i.e., the processing module 124 is configured to perform sound processing on input signals received at the sound processing unit 106). Stated differently, the one or more processors 125 are configured to execute sound processing logic 128 in memory 126 to convert the received input signals into output signals 145 that represent electrical stimulation for delivery to the recipient.

As noted, FIG. 1D illustrates an embodiment in which the processing module 124 in the sound processing unit 106 generates the output signals. In an alternative embodiment, the sound processing unit 106 can send less processed information (e.g., audio data) to the implantable component 112 and the sound processing operations (e.g., conversion of sounds to output signals 145) can be performed by a processor within the implantable component 112. That is, the implantable component 112, rather than the sound processing unit 106, could include a processing module that is similar to processing module 124 of FIG. 1D.

Returning to the specific example of FIG. 1D, the output signals 145 are provided to the RF transceiver 122, which transcutaneously transfers the output signals (e.g., in an encoded manner) to the implantable component 112 via external coil 108 and implantable coil 114. That is, the output signals are received at the RF interface circuitry 140 via implantable coil 114 and provided to the stimulator unit 142. The stimulator unit 142 is configured to utilize the output signals to generate electrical stimulation signals (e.g., current signals) for delivery to the recipient's cochlea via "stimulation channels," where each stimulating channel comprises one or more of the electrodes 144. In this way, cochlear implant system 102 electrically stimulates the recipient's auditory nerve cells, bypassing absent or defective hair cells that normally transduce acoustic vibrations into neural activity, in a manner that causes the recipient to perceive one or more components of the received sound signals.

As noted above, the closely-coupled wireless RF link 131 formed between the external coil 108 and the implantable coil 114 may be used to transfer power and/or data from the external component 104 to the cochlear implant 112. In certain examples, the power and data are transmitted using a modulation technique in which the data is modulated onto the power signals. In the example of FIGS. 1A and 1B, the external coil 108 and at least a portion of the RF transceiver 122 form an external resonant circuit (e.g., external resonant tank circuit) 154. Similarly, the implantable coil 122 and at least a portion of the internal RF interface circuitry 140 form an implantable resonant circuit (e.g., internal resonant tank circuit) 156. The external resonant tank circuit 154 and the internal resonant tank circuit 156 collectively form a resonant system which functions as the bidirectional closely-coupled wireless RF link 131.

In general, the closely-coupled wireless RF link 131 operates at a predetermined operating/center frequency (e.g., approximately 5 MHz RF link) to transfer the power, and potentially data, between the inductive coupled external RF coil 108 and the implantable RF coil 114. However, in conventional arrangements, the signals emitted by the external coil 108 are not only at the operating frequency, but instead also include harmonic transmissions (e.g., transmissions at multiples of the link operating frequency). The harmonic emissions are due, at least in part, to the use of driving the transmission coil with monophasic pulses generated by a single drive. The harmonic emissions may interfere or block desired signals in nearby implantable radio receiver systems. For example, in certain embodiments, the cochlear implant system 102 also includes a magnetic induction (MI) radio receiver (120) that is sensitive to this kind of interference (e.g., the MI signal is weak and there is no provision of steep input filtering (selectivity) on the receiver).

Figure 2A:
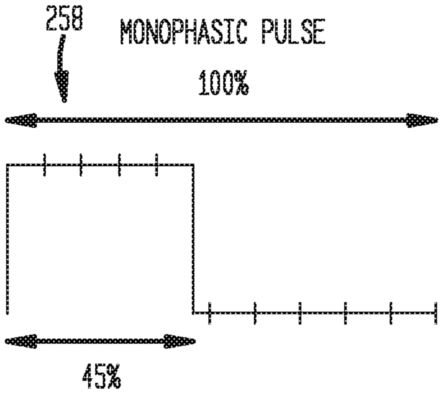
FIG. 2A is a time signal diagram illustrating an example monophasic pulse used to drive a power transmission coil.

FIG. 2A is a time signal diagram illustrating an example monophasic pulse 258 used to drive a transmission coil, in accordance with certain conventional arrangements. In this example, the monophasic pulse 258 has a forty-five (45) percent (%) duty cycle (e.g., the pulse is high or "1" for 45% of the total time, indicated as 100%). In other words, FIG. 2A is a time domain representation of a single amplifier output.

Figure 2B:
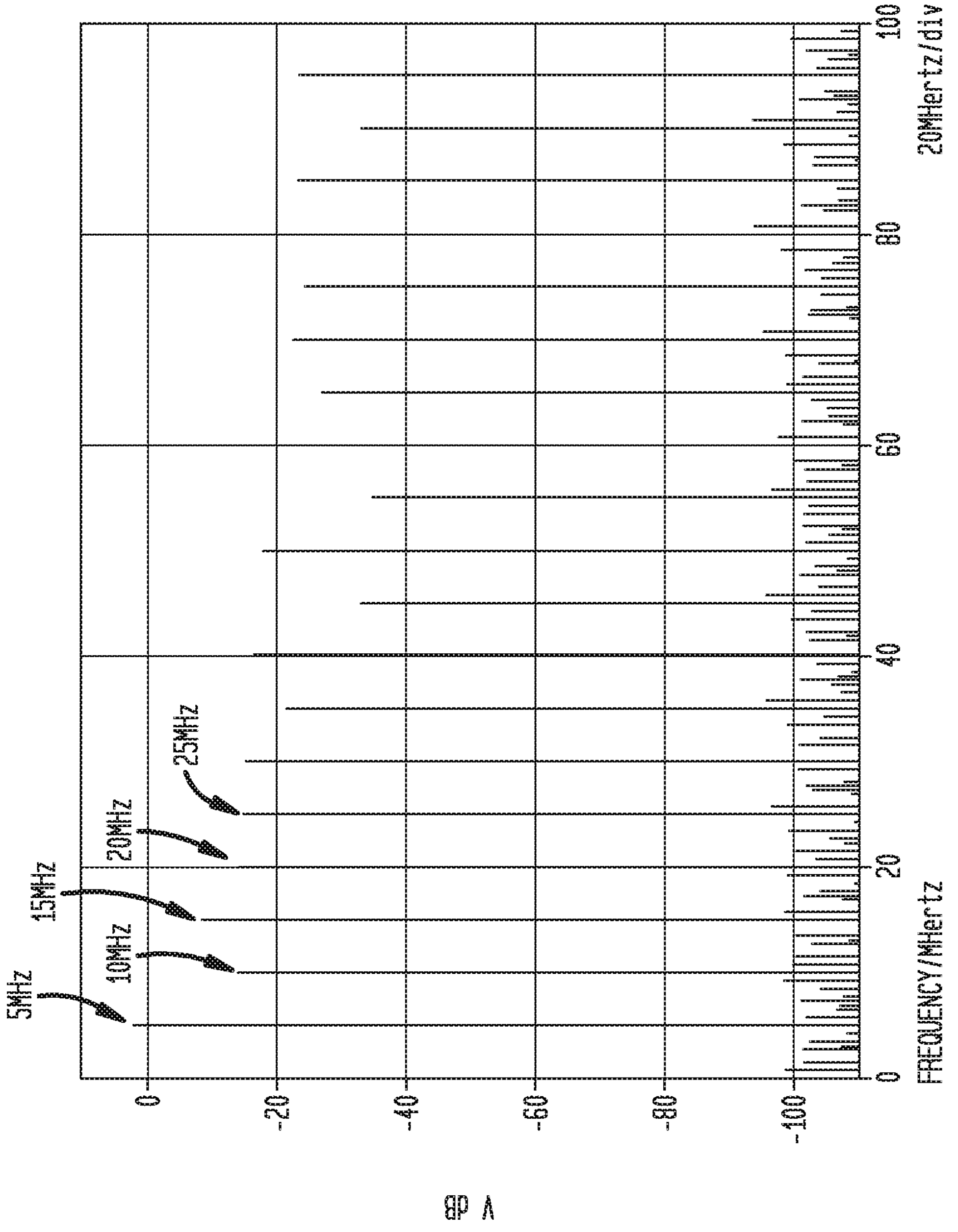
FIG. 2B is a spectral diagram illustrating the frequency spectrum associated with emissions of/by a power transmission coil driven with the monophasic pulse of FIG. 2A.

FIG. 2B is a spectral diagram illustrating the frequency spectrum associated with emissions of/by a transmission coil driven with the monophasic pulse 258 of FIG. 2A via the single amplifier operating at 5 MHz (e.g., pulses with 45% duty cycle (90 ns high)). As shown in FIG. 2B, there is a peak at around 5 MHz, which corresponds to the operating frequency of the link. However, also as shown in FIG. 2B, the spectrum includes harmonic emissions at, for example, 10 MHz, 15 MHz, 10 MHz, 25 MHz, 20 MHz, etc. In conventional arrangements, the nearby radio receiver systems for data transfer need to set away from the harmonics of the power transmission link (e.g., set the MI radio receiver systems to operate at or near 7.5 MHz, 12.5 MHz, 17.5 MHz, 22.5 MHz, 27.5 MHz, etc., when the RF link transmits power at around 5 MHz). However, the limited selectivity and linearity of the MI radio receiver may still be impacted by the nearby harmonic components which could cause saturation of the radio receiver chain.

Accordingly, presented herein are techniques to reduce, minimize, or substantially eliminate one or more selected/predetermined harmonic emissions associated with operation of an inductive power transfer link. That is, one or more selected harmonic emissions associated with operation of an inductive power transfer link are reduced below a threshold level relative to the fundamental frequency. For example, in certain embodiments, one or more selected harmonic emissions are at least 30 dB—below the peak at the fundamental (operating) frequency. In further embodiments, one or more selected harmonic emissions are at least 40 dB below the peak at the fundamental (operating) frequency. In further embodiments, one or more selected harmonic emissions are at least 50 dB below the peak at the fundamental (operating) frequency. In further embodiments, one or more selected harmonic emissions are at least 60 dB below the peak at the fundamental (operating) frequency.

In general, the techniques presented herein drive a plurality of amplifiers with any combination of predefined input pulses in manner that result in the generation and delivery of a "quantized" wave-shaped signal (waveform) to a power transmission (primary) coil. The quantized waveform is a signal having a plurality of discrete levels approximating at least one of a biphasic or sinusoidal shape that, when delivered to a coil, results in a wireless spectrum in which one or more selected harmonic emissions associated with operation of an inductive power transfer link are substantially eliminated. The predefined input pulses are chosen to substantially eliminate one or more selected/predetermined harmonic emissions. The pulse width of each predefined input pulse can be preferably selected such that a predetermined harmonic emission is absent by Fourier analysis. The pulse width of each predefined input pulse and sequence can be preferably selected such that the sum of all pulses approximates at least one of a biphasic or sinusoidal shape.

Figure 3:
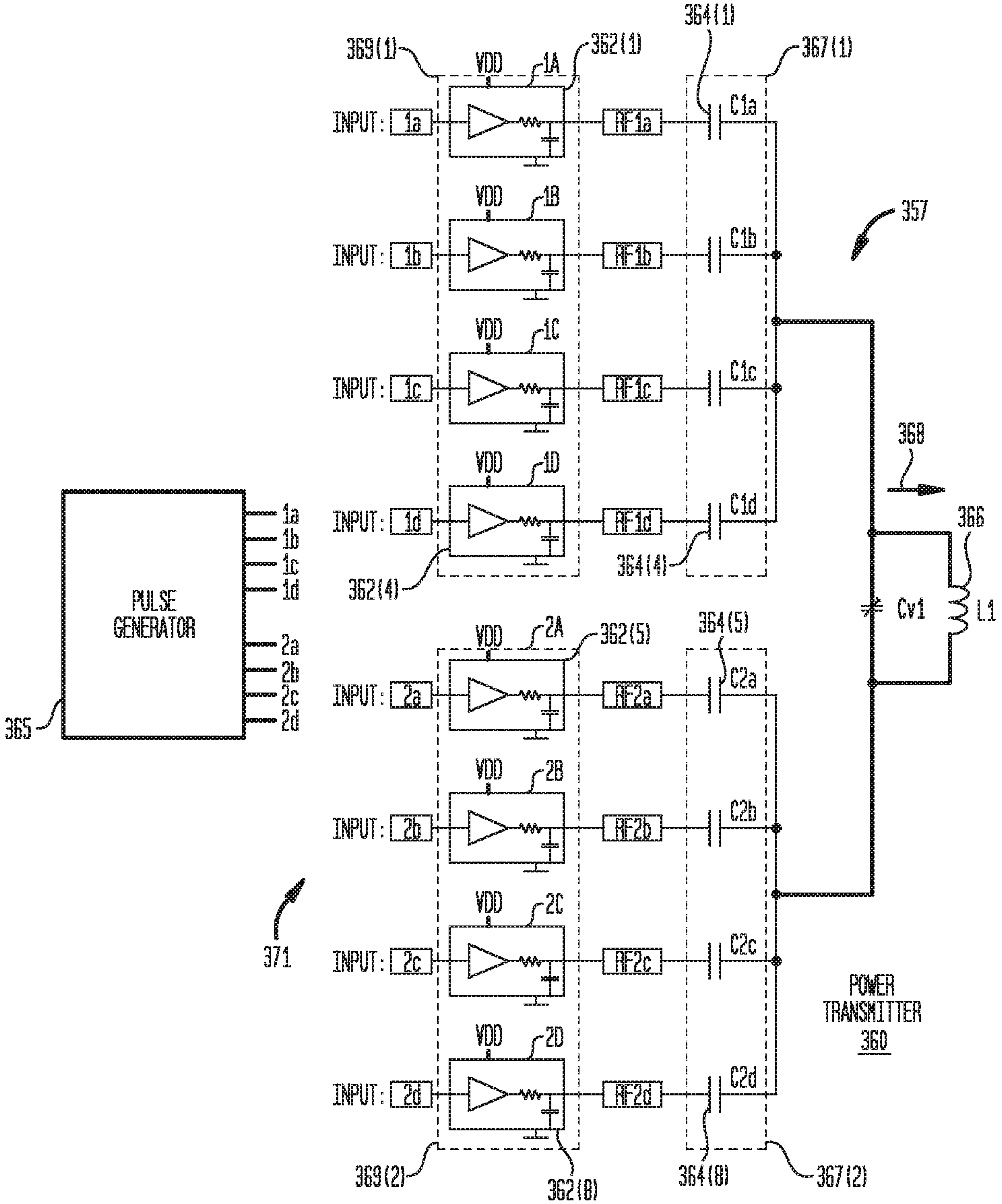
FIG. 3 is a schematic diagram of an example wireless power transmitter unit, in accordance embodiments presented herein.

FIG. 3 is a schematic diagram of an example wireless power transmitter unit 360, in accordance embodiments presented herein. As described elsewhere herein, the wireless power transmitter unit 360 may be integrated into a number of different electronic devices. For example, the wireless power transmitter unit 360 could be implemented as part of the external component 104 of cochlear implant system 102, described above with reference to FIGS. 1A-1D.

The wireless power transmitter unit 360 includes a plurality of amplifiers 362, a plurality of capacitors 364, and a power transmission (primary) coil 366 (L1). In the example of FIG. 3, the plurality of amplifiers 362 comprise eight (8) amplifiers divided into two groups/arrays, referred to as amplifier array 369(1) and 369(2). Each of the amplifier arrays 369(1) and 369(2) includes four (4) half-H-bridges (e.g., Class-D amplifiers). The eight amplifiers are individually referred to as amplifiers 362(1)-362(8). The amplifiers 362(1)-362(8) are driven by a pulse generator 365 with 8 individual outputs and connected to their respective inputs 1A-1D (e.g., amplifiers 362(1)-362(4)) and inputs 2A-2D (e.g., amplifiers 362(5)-362(8)). Each output of the pulse generator 365 may generate one positive predefined pulse per period.

The pulse generator 365 and the plurality of amplifiers 362 collectively form a quantized waveform generator 371. That is, the amplifiers 362(1)-362(8) are independently switched/driven by the pulse generator 365 with selected/predetermined pulse sequences to generate predetermined amplifier output pulse sequences. The amplifier output pulse sequences generated by the amplifiers 362(1)-362(8) are combined such that output pulse sequences collectively form a quantized waveform (e.g., an approximate biphasic shaped or an approximate sinusoidal shaped output signal) 368 having a predetermined associated harmonic emission spectrum. As used herein, a "predetermined associated selected harmonic emission spectrum" means that the quantized waveform, when delivered to the power transmission coil 366, causes the power transmission coil 366 to emit/transmit power signals at a predetermined operating frequency, while substantially eliminating one or more predetermined/selected harmonic or other spurious emissions. In other words, application of a selected pulse sequences at the inputs of the amplifiers 362(1)-862(8) generates an resultant output waveform 368 that, when applied to the coil 866, causes certain harmonic and/or other spurious emissions to be eliminated from the emitted signals, which is advantageous for coexistence with other radio links.

In the example of FIG. 3, the eight amplifiers 362(1)-362(8) are combined with eight tuning capacitors 364, referred to individually as tuning capacitors 364(1)-364(8). The tuning capacitors 364(1)-364(8) are organized into two groups/arrays, referred to as capacitor array 367(1) and 367(2). Each of the capacitor arrays 367(1) and 367(2) includes four (4) capacitors and the capacitors are connected to the power transmission coil 366 in series resonance. In operation, the amplifiers 362(1)-362(8) can be optimized for reduced switching and reducing conductive losses as the capacitor arrays 367(1) and 367(2) may be spread out over four capacitance values. In certain embodiments, the capacitance of each of the tuning capacitors 364(1)-364(8) is equal. In other embodiments, the capacitance of each of the tuning capacitors 364(1)-364(8) is binary scaled. In certain embodiments, the amplitude of the current is spread equally over the tuning capacitors 364(1)-364(8), even when applying different input pulses and the sum of these currents flow though the coil 366.

Figure 4A:
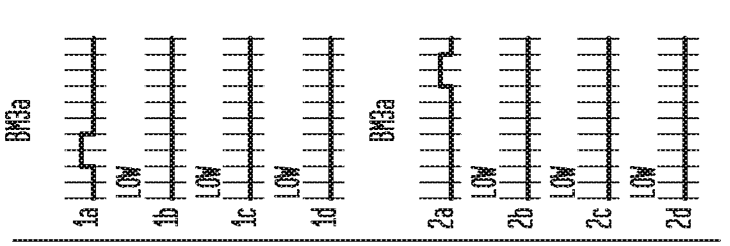
FIGS. 4A to 4N are time signal diagrams illustrating example specific pulse sequences that can be delivered to the inputs of a plurality of Class-D amplifiers of FIG. 3, in accordance with certain embodiments presented herein.
Figure 4B:
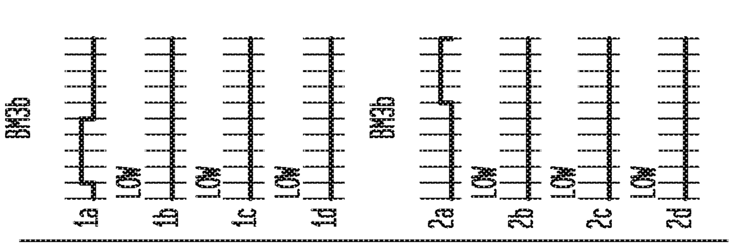
Figure 4C:
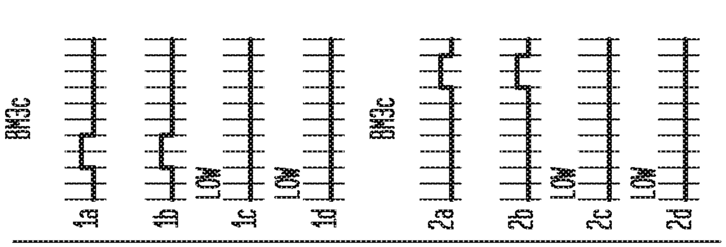
Figure 4D:
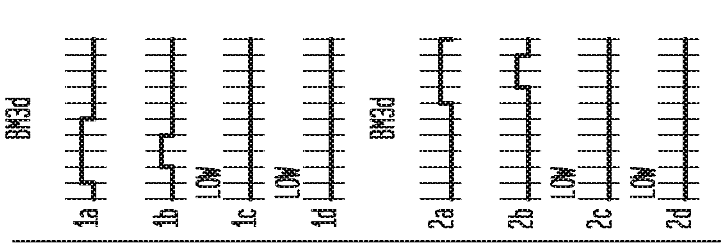
Figure 4E:
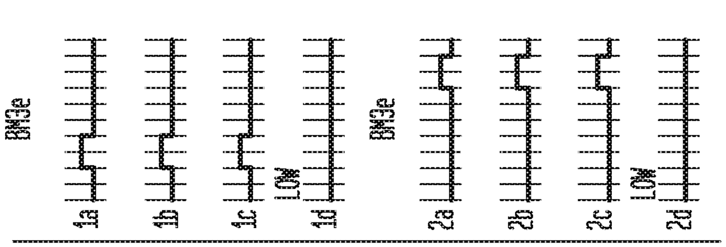
Figure 4F:
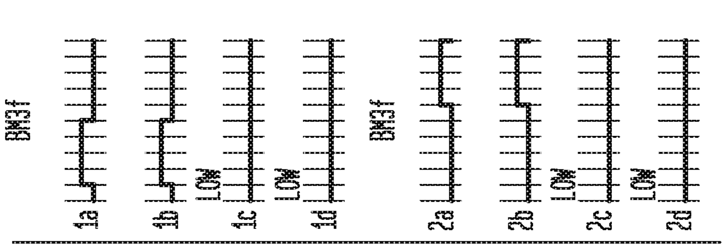
Figure 4G:
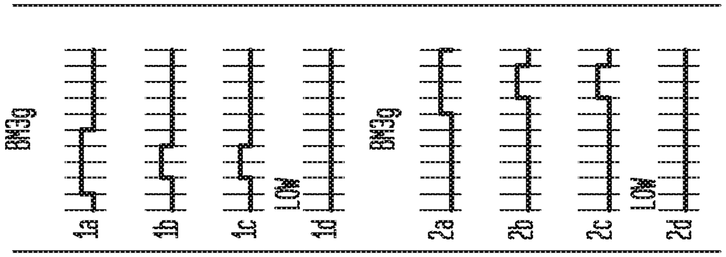
Figures 4H, 4I, 4J, 4K, 4L, 4M, 4N:
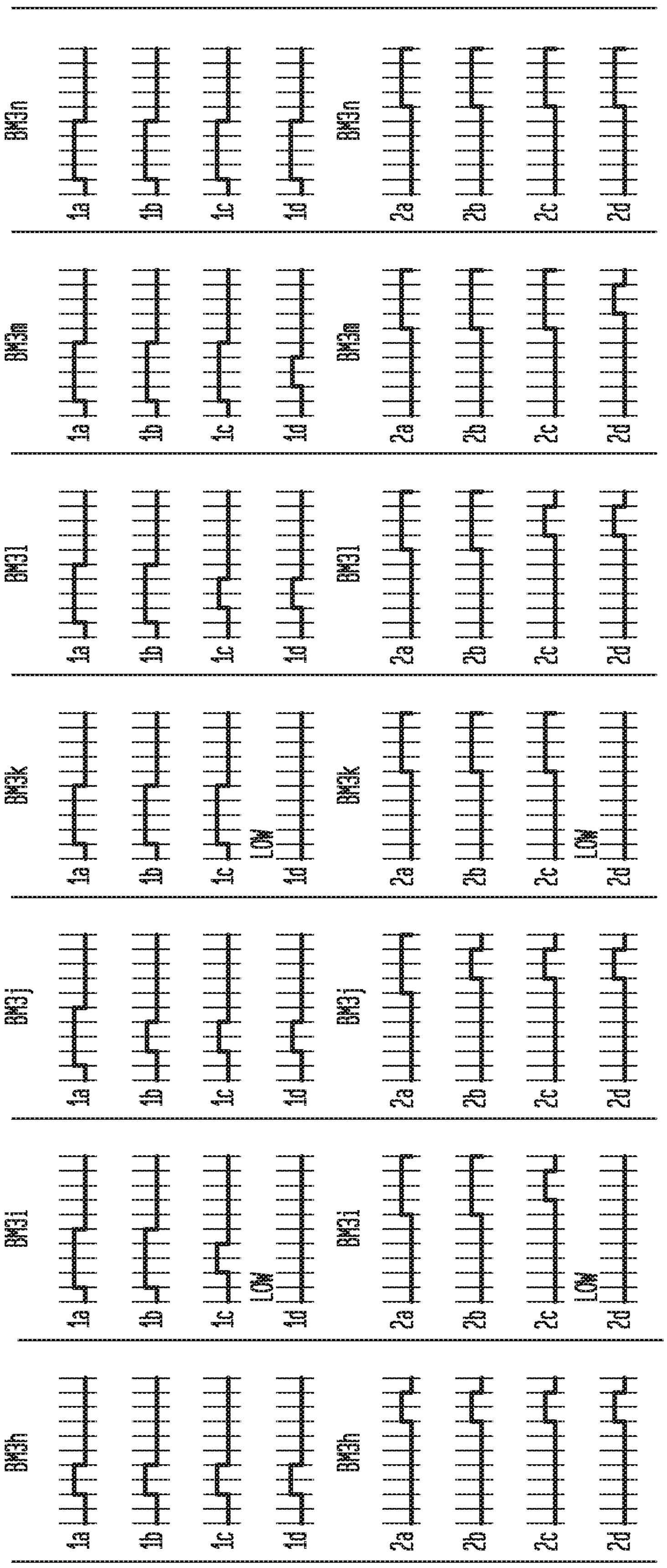

As noted above, a specific sequence of pulses is applied on the inputs of the amplifiers 362(1)-362(8) to generate a quantized waveform (e.g., a biphasic or an approximate sinusoidal wave shaped output signal) 368 having a predetermined associated harmonic emission spectrum, meaning that one or more selected harmonic emissions are missing from the resulting emission generated by the coil 366 in response to the quantized waveform 368. FIGS. 4A-4N illustrate different example combinations of pulse sequences that can be applied to the inputs 1*a*-1*d* (e.g., amplifiers 362(1)-362(4)) and inputs 2*a*-2*d* (e.g., amplifiers 562(5)-362(8)) to generate different quantized waveforms having predetermined associated harmonic emission spectrums. In certain implementations, FIGS. 4A-4N illustrate examples of specific pulse sequences that can be delivered to the inputs 1*a*-1*a* and 2*a*-2*d* of the amplifiers 362(1)-362(8) of FIG. 3 to eliminate the $3^{rd}$ and $5^{th}$ harmonics of a 5 MHz RF link.

Figures 5A, 5B, 5C, 5D, 5E, 5F, 5G, 5H, 5I, 5J, 5K, 5L, 5M, 5N:
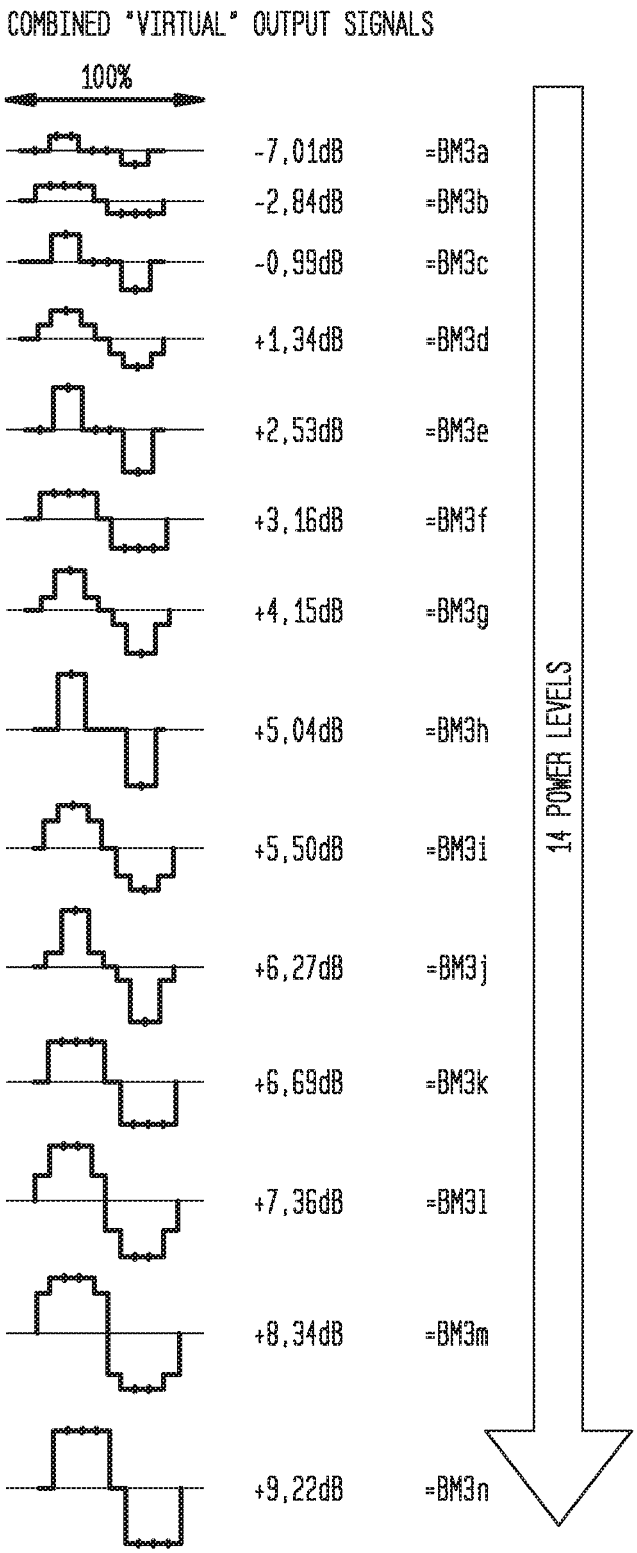
FIGS. 5A to 5N illustrate example quantized waveforms resulting from different combinations of the pulse sequences of FIGS. 4A to 4N, when applied at inputs of a plurality of Class-D amplifiers, in accordance with certain embodiments presented herein.

FIGS. 5A-5N illustrate example quantized waveforms resulting from different combinations of the pulse sequences of FIGS. 4A-4N, when applied at the inputs of the amplifiers 362(1)-362(8) of FIG. 3. In certain examples of FIGS. 5A-5N, the quantized waveforms biphasic wave shapes or "approximate sinusoidal" wave shape. As used herein, an "approximate sinusoidal" wave shape means that the quantized waveform follows general sinusoidal shape, but includes discrete steps therein. The goal of the approximate sinusoidal wave shape is not to create a perfect sinusoidal output signal without harmonics as such a shape would require an infinite number of amplifiers creating huge switching power losses while requiring large numbers of capacitors and other circuit components. Instead, the approximate sinusoidal wave shape is sufficient to reduce or substantially eliminate one or more harmonics of the operating frequency, which would be sufficient to ensure compatibility with nearby radio receivers.

FIGS. 6A to 6L are time signal diagrams illustrating other example specific pulse sequences that can be delivered to the inputs of a plurality of Class-D amplifiers of FIG. 3, in accordance with certain embodiments presented herein.

FIGS. 6A to 6L illustrate other example specific combination of pulse sequences that can be applied to the inputs 1*a*-1*d* (e.g., amplifiers 362(1)-362(4)) and inputs 2*a*-2*d* (e.g., amplifiers 562(5)-362(8)) to generate different quantized waveforms having predetermined associated harmonic emission spectrums. In certain implementations, FIGS. 6A-6L illustrate examples of specific pulse sequences (some shifted in time) wherein the $4^{th}$ and 5th harmonic may not be fully eliminated, but the quantized waveform is more sinusoidal . . . FIGS. 7A to 7L illustrate example quantized waveforms resulting from different combinations of the pulse sequences of FIGS. 6A-6L, when applied at the inputs of the amplifiers 362(1)-362(8) of FIG. 3.

Figure 8A:
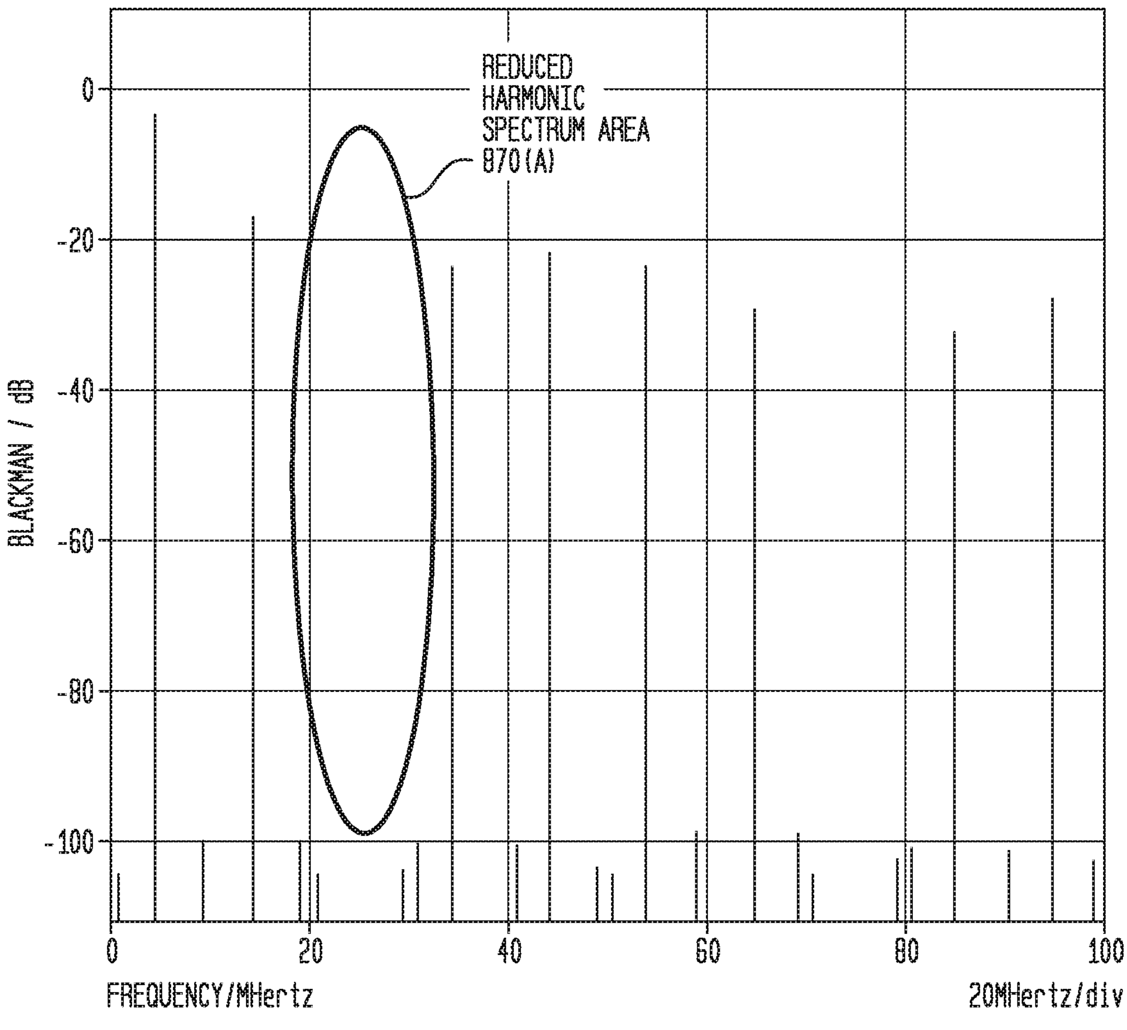
FIG. 8A is a spectral diagram illustrating the spectrum associated with emissions of/by a power transmission coil when driven with the quantized waveform of FIG. 5B.

FIG. 8A is a spectral diagram illustrating the frequency spectrum associated with emissions of/by the power transmission coil 366 when driven with a quantized waveform as generated by the plurality of amplifiers 362(1)-362(8) of FIG. 3 at 5 MHz with the predefined pulses of FIG. 5B. As shown in FIG. 8A, there is a peak at around 5 MHz, which corresponds to the operating frequency of the RF link. However, also as shown in FIG. 8A, the spectrum includes one or more reduced harmonic spectrum areas 870(A) where the $5^{th}$ harmonic, and the even harmonics, have been substantially eliminated.

Figure 8B:
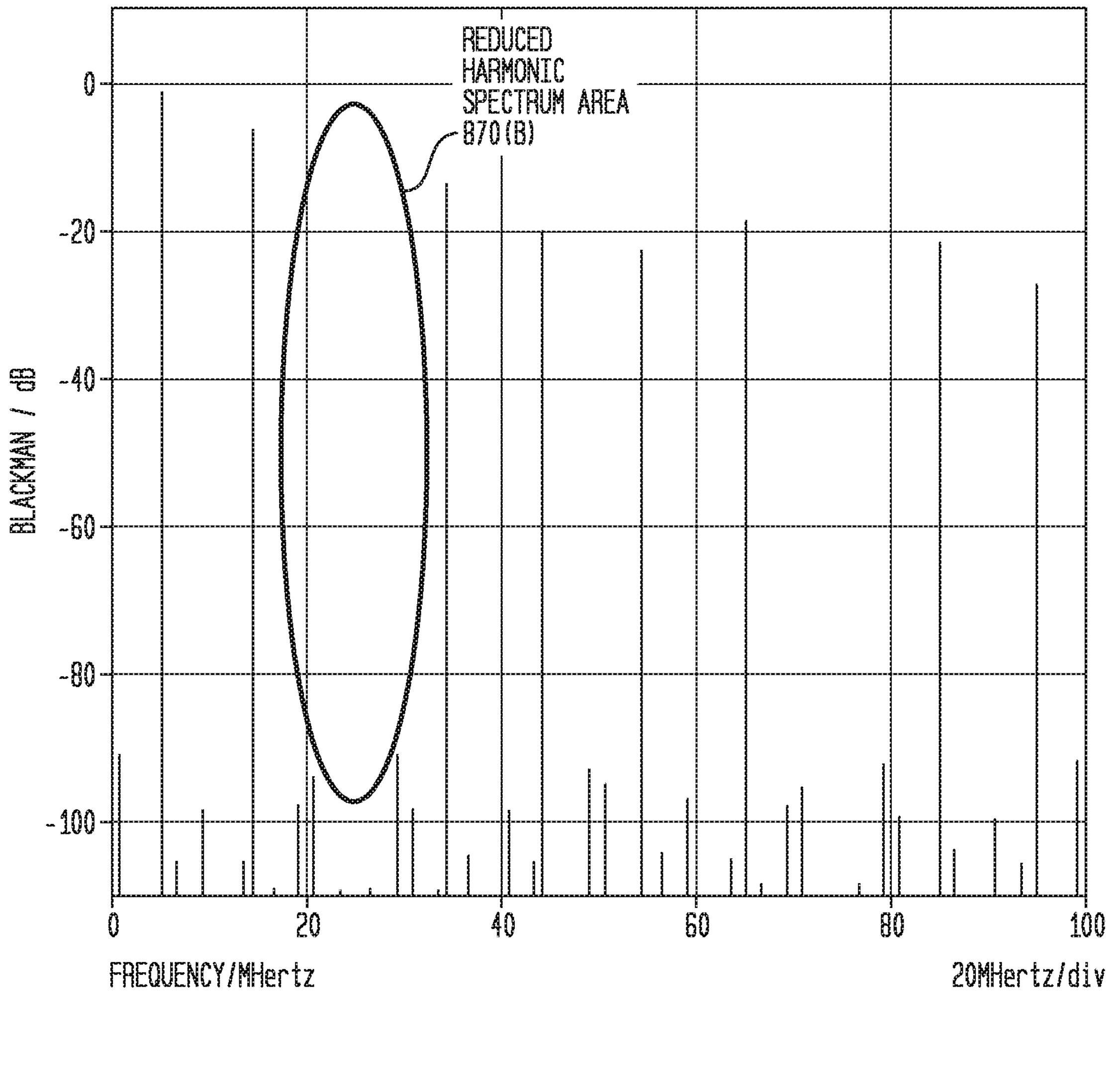
FIG. 8B is a spectral diagram illustrating the frequency spectrum associated with emissions of/by a power transmission coil when driven with the quantized waveform of FIG. 5C.

FIG. 8B is a spectral diagram illustrating the frequency spectrum associated with emissions of/by the power transmission coil 366 when driven with another quantized waveform as generated by the plurality of amplifiers 362(1)-362(8) of FIG. 3 at 5 MHz with the predefined pulses of FIG. 5C. As shown in FIG. 8B, there is a peak at around 5 MHz, which corresponds to the operating frequency of the RF link. However, also as shown in FIG. 8B, the spectrum includes one or more reduced harmonic spectrum areas 870(B) where the $5^{th}$ harmonic, and the even harmonics, have been substantially eliminated.

Figures 6A, 6B, 6C, 6D, 6E, 6F:
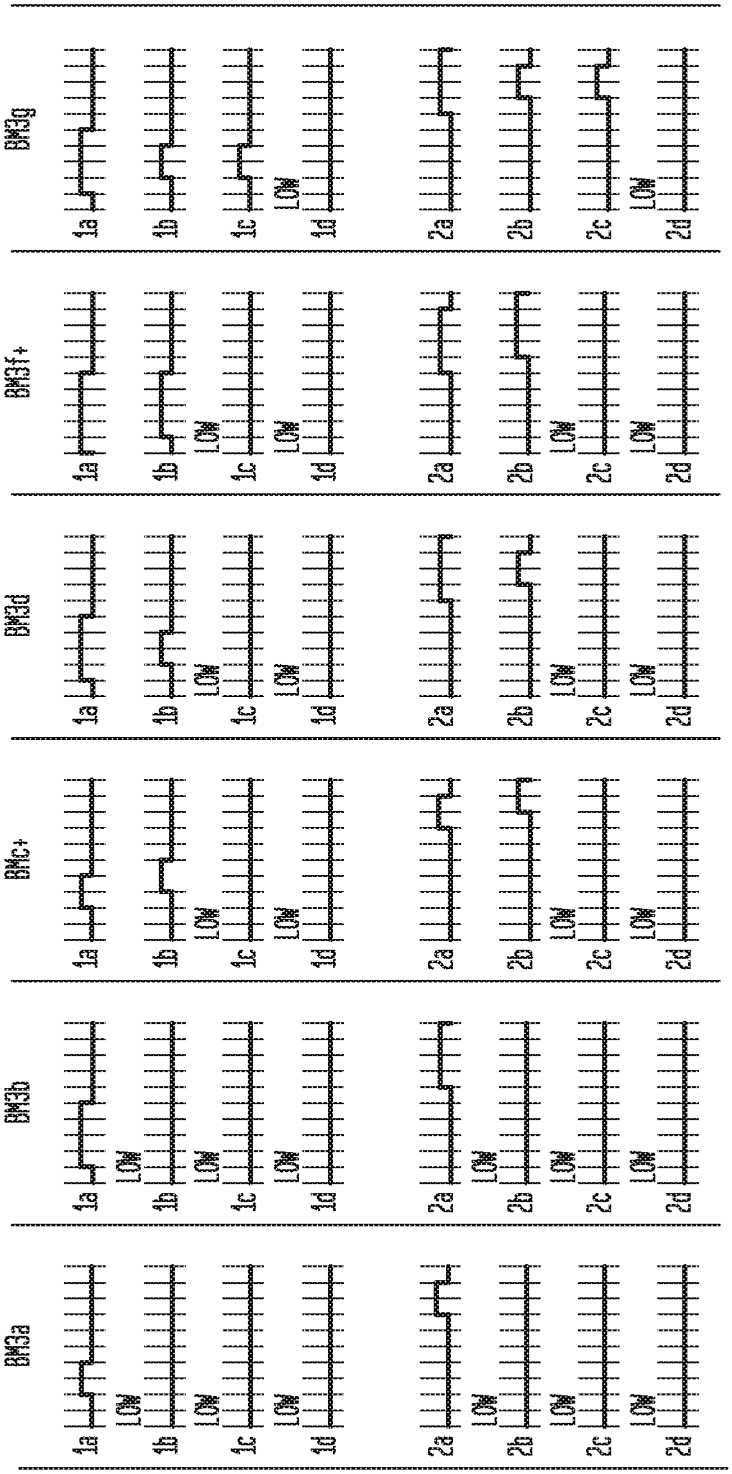
FIGS. 6A to 6L are time signal diagrams illustrating other example specific pulse sequences that can be delivered to the inputs of a plurality of Class-D amplifiers of FIG. 3, in accordance with certain embodiments presented herein.
Figures 6G, 6H, 6I, 6J, 6K, 6L:
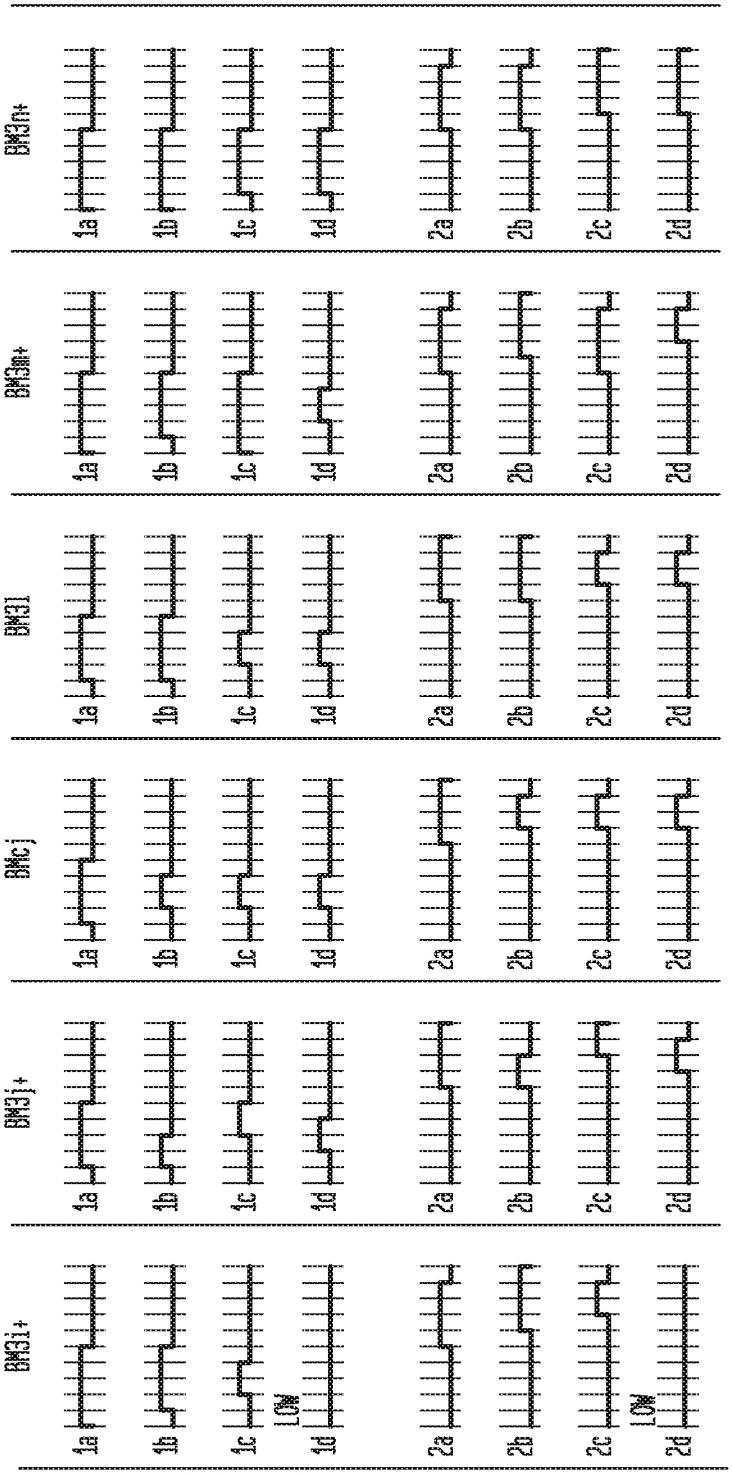
Figures 7A, 7B, 7C, 7D, 7E, 7F, 7G, 7H, 7I, 7J, 7K, 7L:
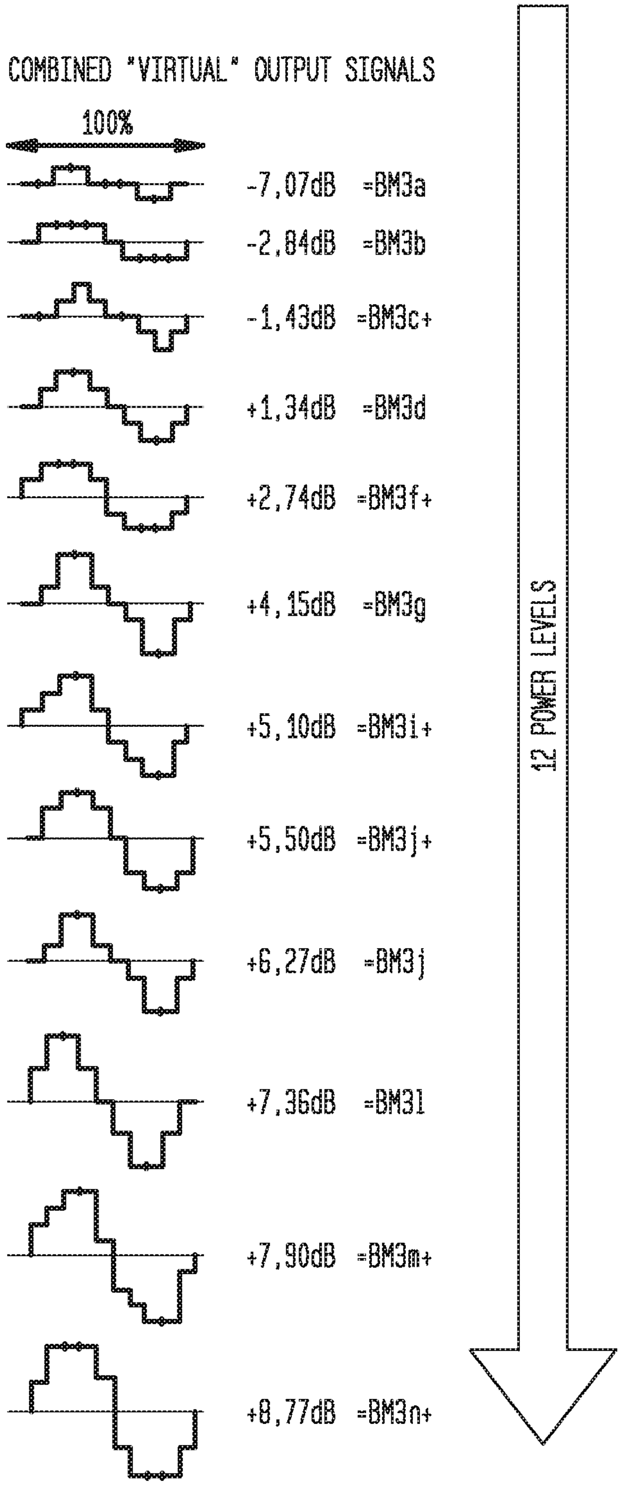
FIGS. 7A to 7L illustrate example optimized quantized waveforms resulting from different combinations of the pulse sequences of FIGS. 6A to 6N, when applied at inputs of a plurality of Class-D amplifiers, in accordance with certain embodiments presented herein.
Figure 8C:
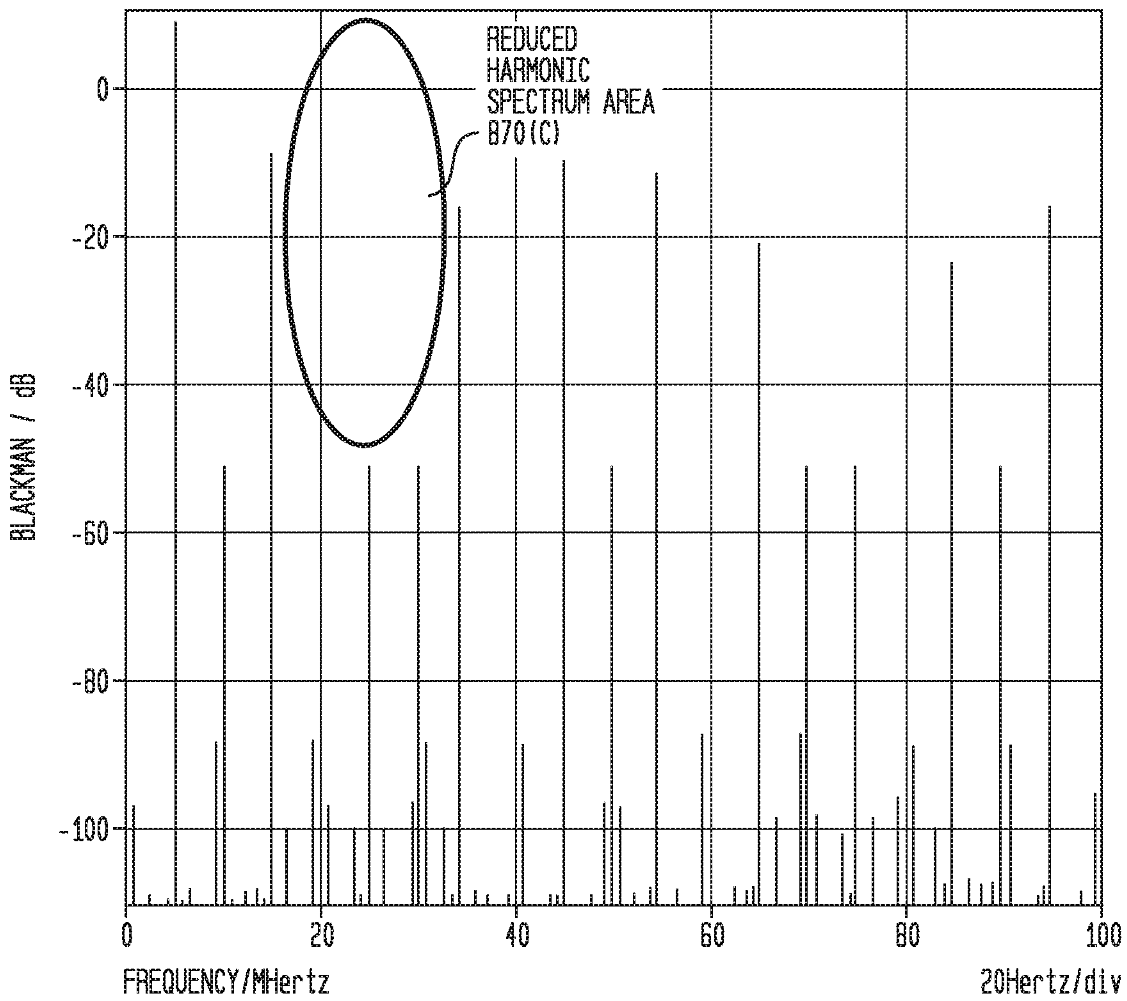
FIG. 8C is a spectral diagram illustrating the spectrum associated with emissions of/by a power transmission coil when driven with the quantized waveform of FIG. 7L.

FIG. 8C is a spectral diagram illustrating the frequency spectrum associated with emissions of/by the power transmission coil 366 when driven with another quantized waveform as generated by the plurality of amplifiers 362(1)-362(8) of FIG. 3 at 5 MHz with the predefined pulses of FIG. 6L. As shown in FIG. 8C, there is a peak at around 5 MHz, which corresponds to the operating frequency of the RF link. However, also as shown in FIG. 8C, the spectrum includes one or more reduced harmonic spectrum areas 870(C) where the $5^{th}$ harmonic, and the even harmonics, have been substantially eliminated.

Figure 9A:
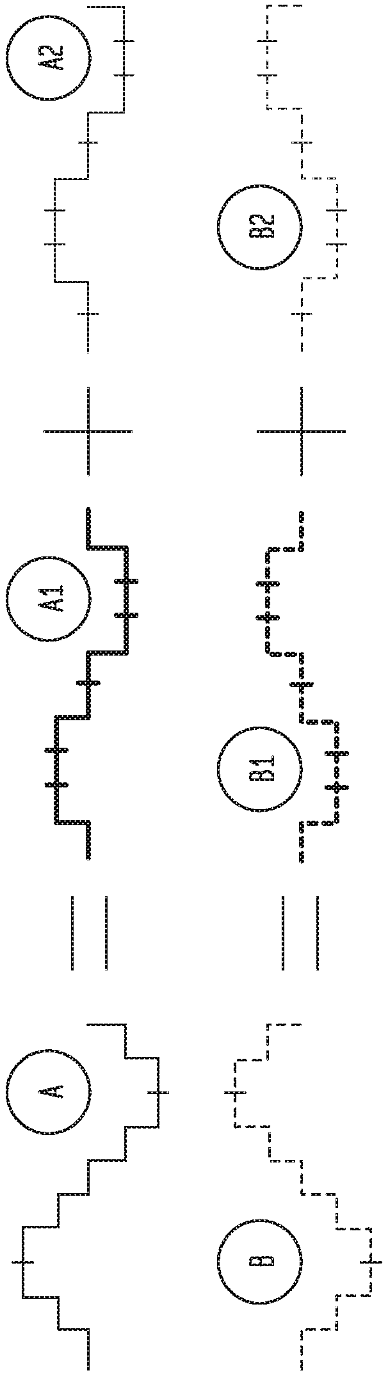
FIG. 9A is a time signal diagram illustrating two 5-step quantized waveforms, and combinations of 3-step symmetrical pulse sequences to construct the two 5-step quantized waveforms, in accordance with certain embodiments presented herein.

As noted above, quantized waveforms in accordance with embodiments presented herein having an approximate sinusoidal wave shape having different numbers of discrete levels. In on example, the quantized waveform has five (5) discrete steps/levels that can be generated using different combinations of inputs at the amplifiers 362(1)-362(8) of FIG. 3. As shown in FIG. 9A, the 5-step quantized waveform is a symmetric waveform and can comprise a cathodic phase followed by an anodic phase, labeled in FIG. 9A as quantized waveform (A), or the waveform can comprise an anodic phase followed by a cathodic phase, labeled in FIG. 9A as quantized waveform (B). Also as shown in FIG. 9A, the 5-step quantized waveforms (A) and (B) can be constructed by a summation or subtraction of two 3-step symmetrical pulse sequences. As shown, two 3-step symmetrical pulse sequences labeled as symmetrical pulse sequences (A1) and (A2) can be used to construct the quantized waveform (A), while two 3-step symmetrical pulse sequences labeled as symmetrical pulse sequences (B1) and (B2) can be used to construct the quantized waveform (B).

Figure 9B:
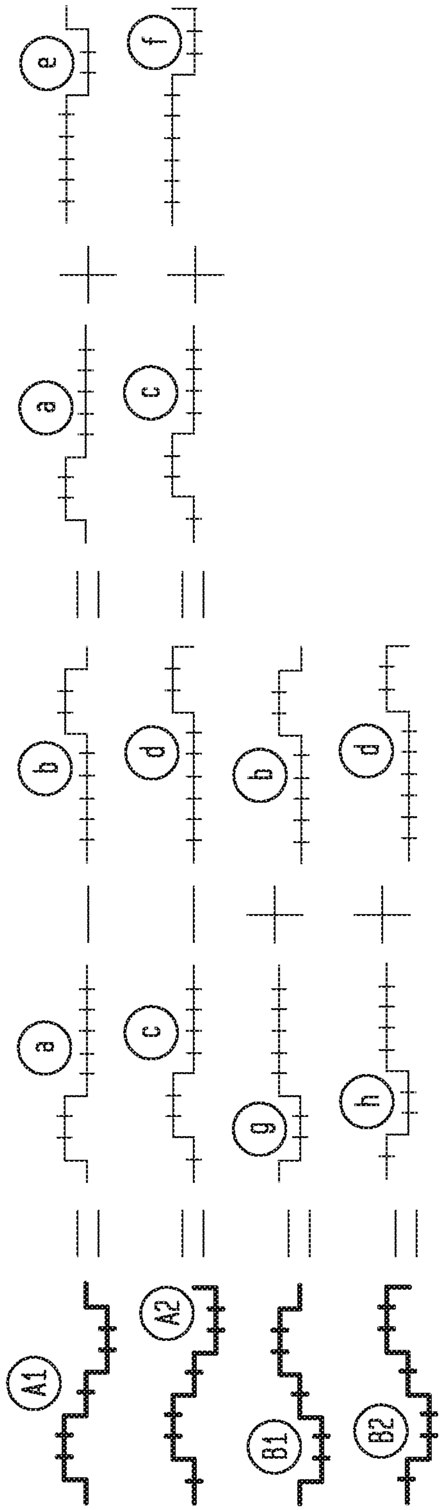
FIG. 9B is a time signal diagram illustrating the 3-step symmetrical pulse sequences of FIG. 9A and combinations of 2-step symmetrical pulse sequences to construct the 3-step symmetrical pulse sequences, in accordance with certain embodiments presented herein.

Moreover, as shown in FIG. 9B, the 3-step symmetrical pulse sequences of FIG. 9A (i.e., (A1), (A2), (B1), and (B2)) can be constructed by a summation or a subtraction of two 2-step symmetrical pulse sequences generated via a plurality of amplifiers (e.g., amplifier 362(1)-362(8) of FIG. 3). In FIG. 9B, the 2-step symmetrical pulse sequences used to construct the 3-step symmetrical pulse sequences of FIG. 7A (i.e., (A1), (A2), (B1), and (B2) are labeled as pulse sequences (a), (b), (c), (d), (e), (f), (g), and (h). FIG. 9B illustrates the various combinations of the 2-step symmetrical pulse sequences (a), (b), (c), (d), (e), (f), (g), and (h) that can be used to construct each of the 3-step symmetrical pulse sequences of FIG. 9A.

Figure 9C:
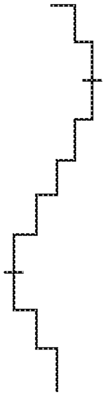
FIG. 9C is a table summarizing the examples of FIGS. 9A and 9B.
Figure 9C:
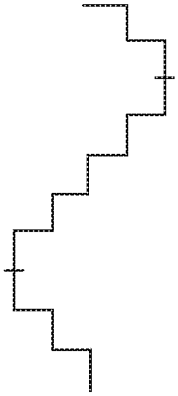
Figure 9C:
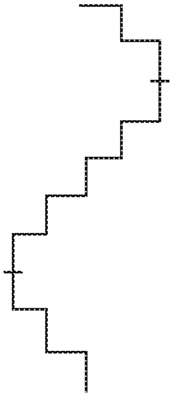

FIG. 9C is a table summarizing FIGS. 9A and 9B where each of the sequences are applied in the example arrangement of FIG. 3 to generate different quantized waveforms. More specifically, the table of FIG. 9C includes a first column indicating the bridges 362(1)-362(8), and a second column identifying a given 2-step pulse sequence (a), (b), (c), (d), (e), (f), (g), and (h) that is applied at the bridges identified in column 1. The table of FIG. 9C includes a third column identifying the 3-step symmetrical pulse sequences constructed by the combinations of applied 2-step pulses. The 3-step symmetrical pulse sequences shown in FIG. 9C result in various quantized waveforms, as discussed above, and as identified in the fourth column of FIG. 9C.

Embodiments have generally been described above with reference to an embodiment in which the wireless power transmitter comprises eight (8) amplifiers arrangement into two groups or arrays, with eight (8) capacitors in series resonance with the power transmission coil. It is to be appreciated that this specific arrangement is merely illustrative and that the techniques presented herein can be implemented with different numbers of amplifiers, different groups of amplifiers, different numbers of capacitors, etc.

Figure 10:
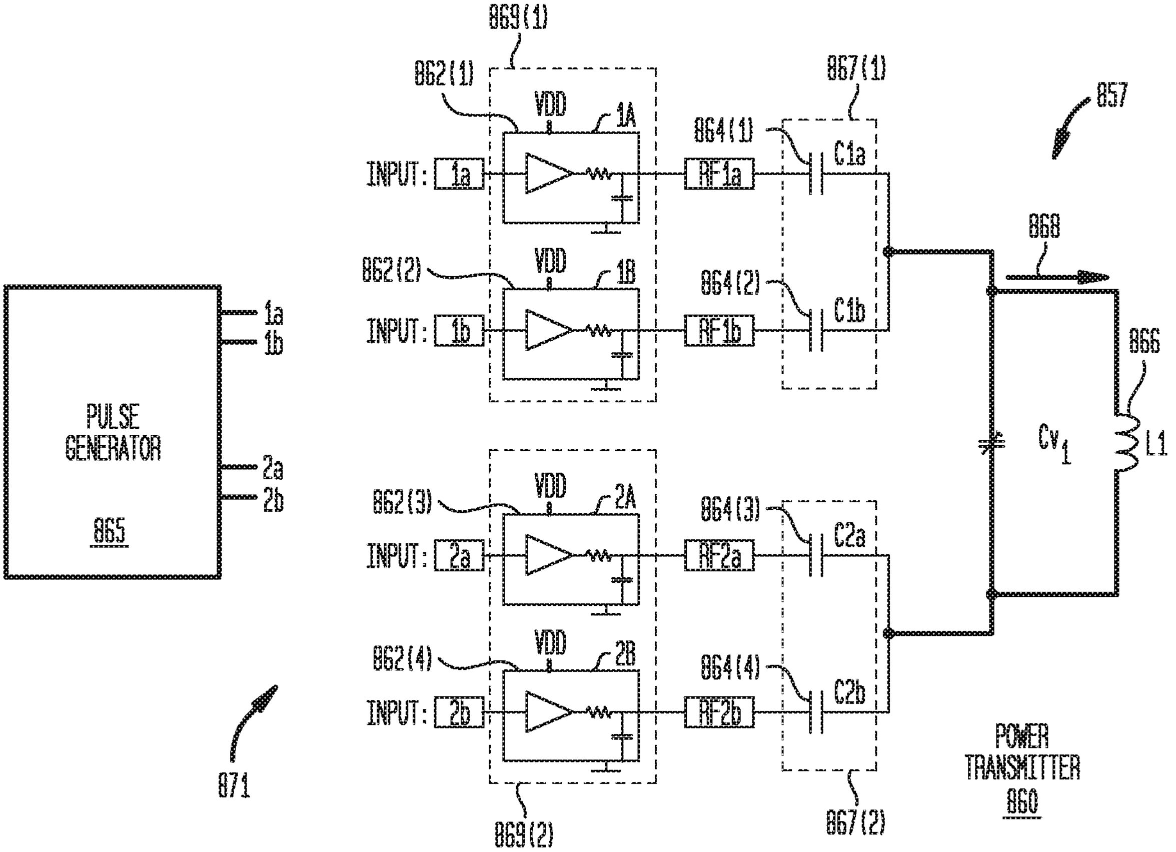
FIG. 10 is a schematic diagram of an example wireless power transmitter unit using two groups of amplifiers, in accordance embodiments presented herein.
Figure 11A:
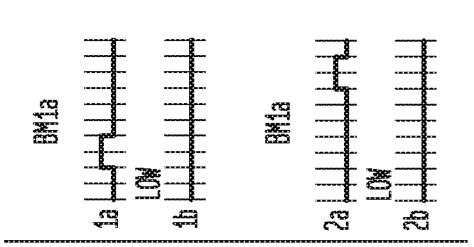
FIGS. 11A, 11B, 11C, 11D, and 11E are time signal diagrams illustrating different example combinations of pulse sequences that can be applied to the inputs of a plurality of Class-D amplifiers of FIG. 10, in accordance with certain embodiments presented herein.
Figure 11B:
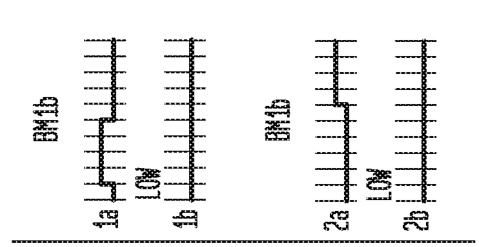
Figure 11C:
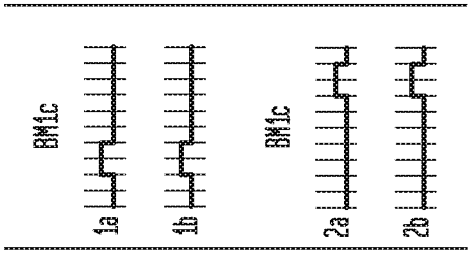
Figure 11D:
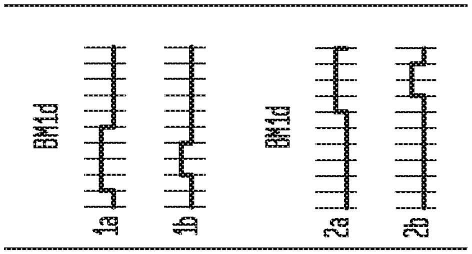
Figure 11E:
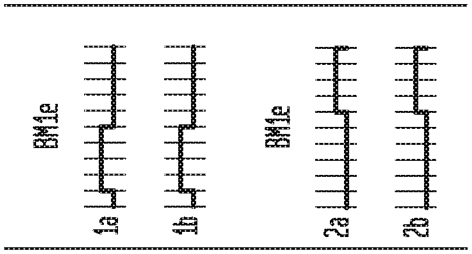

For example, FIG. 10 is a schematic diagram of an example wireless power transmitter unit 860 including two groups of amplifiers, in accordance embodiments presented herein. In this example, the wireless power transmitter unit 860 includes four (4) amplifiers 862(1)-862(4), four capacitors 864(1)-864(4), and a power transmission (primary) coil 866 (L1). In the example of FIG. 10, the amplifiers 862(1)-862(4) are divided into two groups/arrays, referred to as amplifier array 869(1) and 869(2), that each include two (2) half-H-bridges (e.g., Class-D amplifiers). The amplifiers 862(1)-862(4) are driven by a pulse generator 865 via respective inputs 1*a*-1*b* (e.g., amplifiers 862(1) and 862(2)) and inputs 2*a*-2*a* (e.g., amplifiers 862(3) and 862(4)). Each output of the pulse generator 865 may generate one positive predefined pulse per period.

The pulse generator 865 and the 862(1)-862(4) collectively form a quantized waveform generator 871. That is, the amplifiers 862(1)-862(4) are independently switched/driven by the pulse generator 865 with selected/predetermined pulse sequences to generate predetermined amplifier output pulse sequences. The amplifier output pulse sequences generated by the amplifiers 862(1)-862(4) are combined such that output pulse sequences collectively form a quantized waveform (e.g., biphasic or an approximate sinusoidal shaped output signal) 868 having a predetermined associated harmonic emission spectrum. That is, when the quantized waveform 868, when delivered to the power transmission coil 866, causes the power transmission coil 866 to emit/transmit power signals at a predetermined operating frequency, while eliminating one or more predetermined/selected harmonic or other spurious emissions. In other words, application of a selected pulse sequences at the inputs of the amplifiers 862(1)-862(4) generates an resultant output waveform that, when applied to the coil 866, causes certain harmonic and/or other spurious emissions to be missing from the emitted signals, which is advantageous for coexistence with other radio links.

In the example of FIG. 10, the four amplifiers 862(1)-862(4) are combined with four tuning capacitors 864(1)-864(4). The tuning capacitors 864(1)-864(4) are organized into two groups/arrays, referred to as capacitor array 867(1) and 867(2), that each include two (2) capacitors. The tuning capacitors 864(1)-864(4) are connected to the power transmission coil 866 in series resonance.

As noted above, a specific sequence of pulses is applied on the inputs of the amplifiers 862(1)-862(4) to generate a quantized waveform (e.g., a biphasic or an approximate sinusoidal wave shaped output signal) 868 having a predetermined associated harmonic emission spectrum, meaning that one or more selected harmonic emissions are missing from the resulting emission generated by the coil 866 in response to the quantized waveform 868. FIGS. 11A, 11B, 11C, 11D, and 11E illustrate different example combinations of pulse sequences that can be applied to the inputs 1*a*-1*b* (e.g., amplifiers 862(1) and 862(2)) and inputs 2*a*-2*b* (e.g., amplifiers 862(3) and 862(4)) to generate different quantized waveforms having predetermined associated harmonic emission spectrums.

Figure 12:
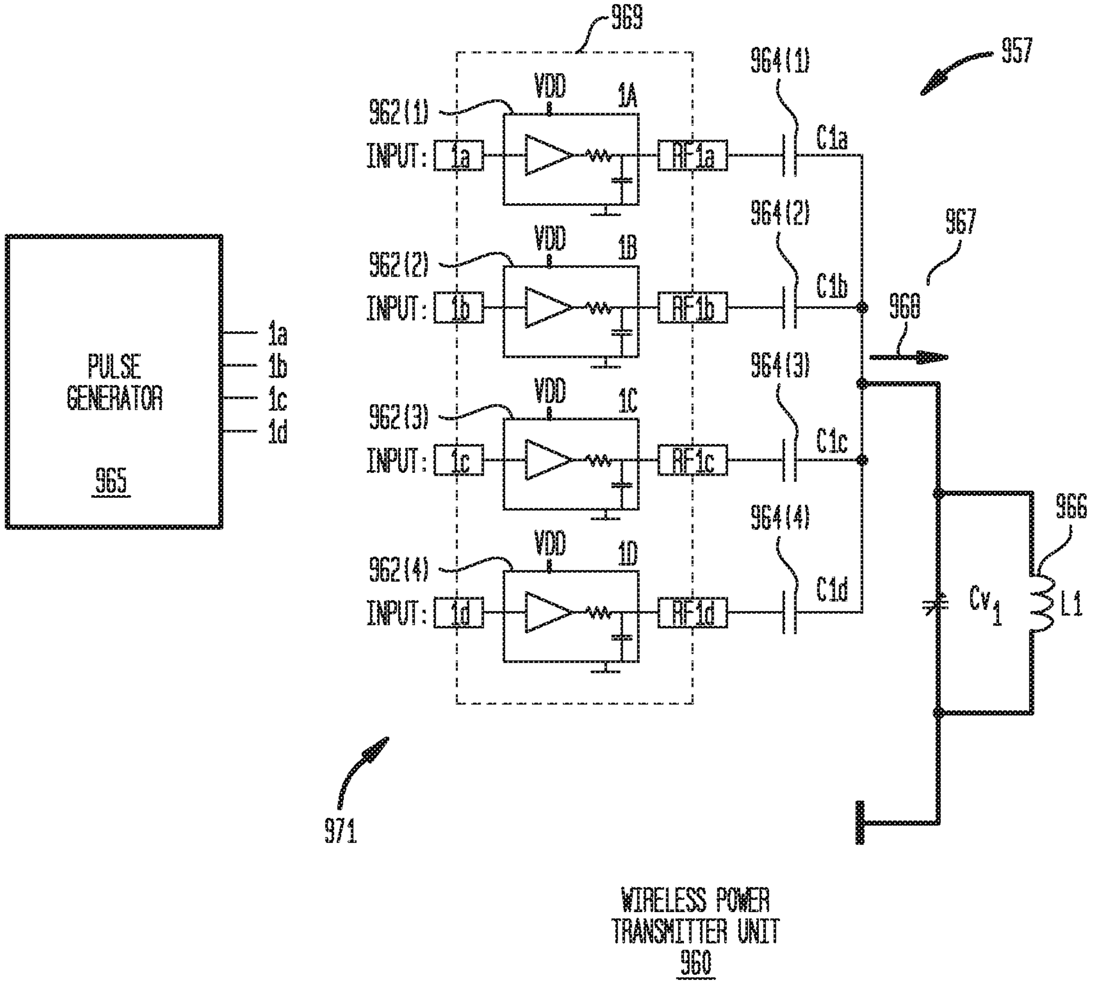
FIG. 12 is a schematic diagram of an example wireless power transmitter unit using a single group of amplifiers, in accordance embodiments presented herein.
Figure 13:
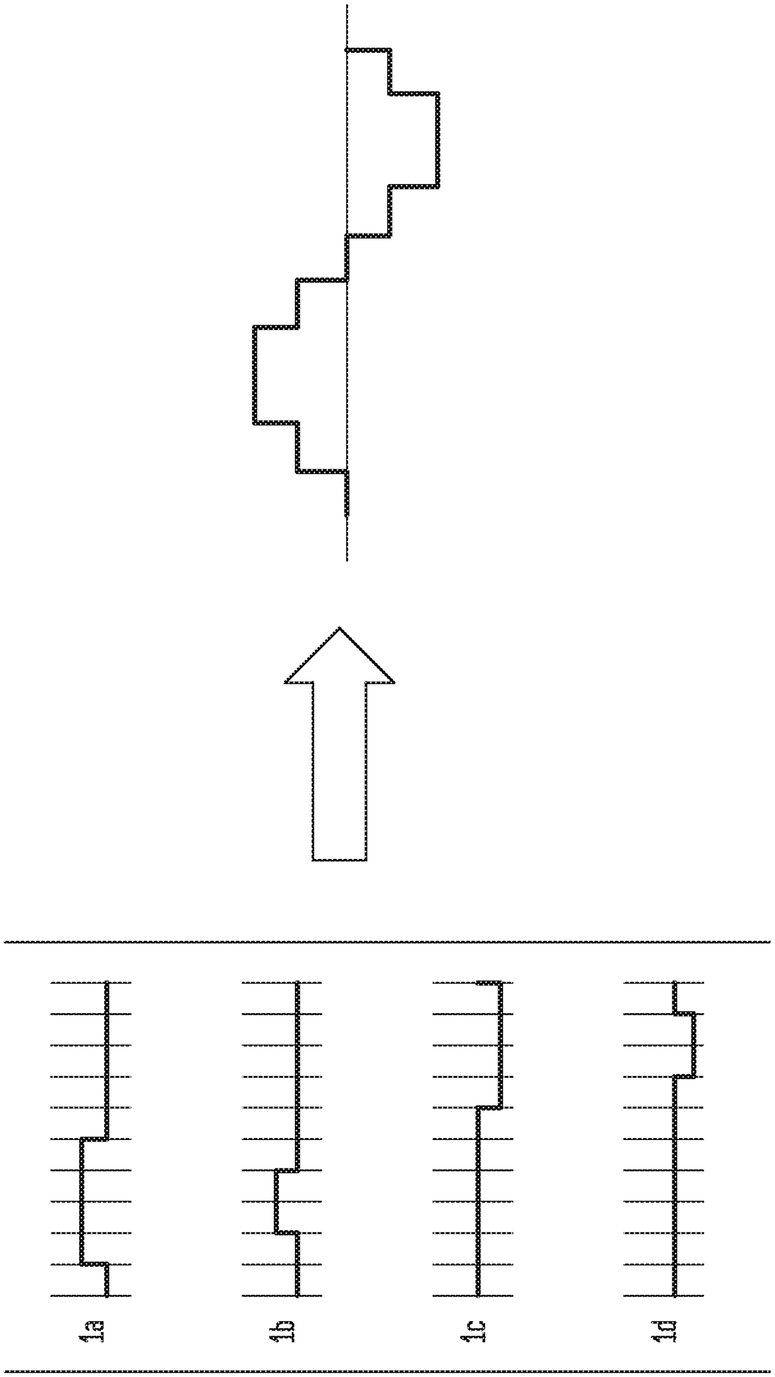
FIG. 13 is a time signal diagrams illustrating an example combinations of pulse sequences that can be applied to the inputs of a group of amplifiers of FIG. 12, in accordance with certain embodiments presented herein.

FIG. 12 is a schematic diagram of an example wireless power transmitter unit 960 including a single group of amplifiers, in accordance embodiments presented herein. FIG. 13 illustrates an example combinations of pulse sequences that can be applied to the inputs 1*a*-1*d* (e.g., amplifiers 962(1) to 962(3)) to generate different quantized waveforms having predetermined associated harmonic emission spectrums.

Figure 14:
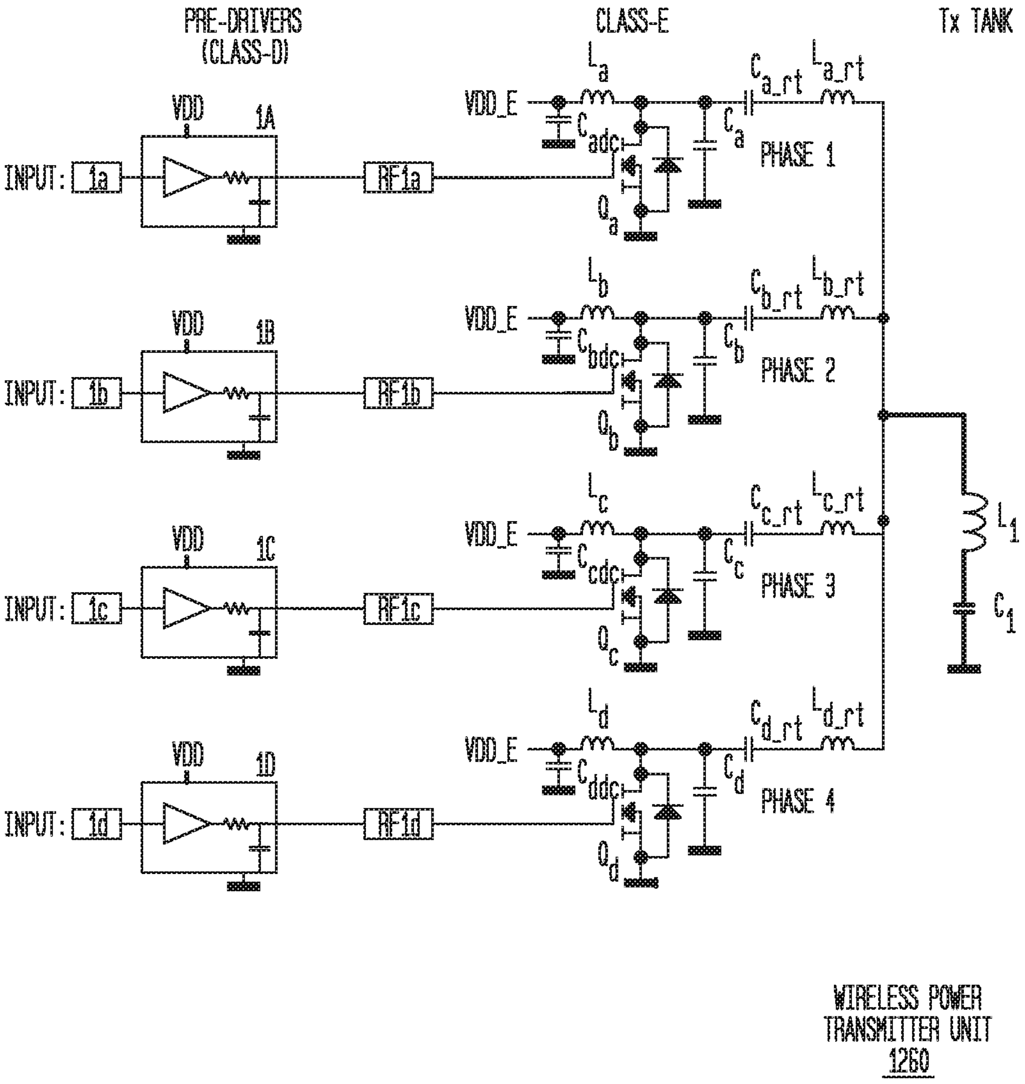
FIG. 14 is a schematic diagram illustrating a plurality of Class-E amplifiers, in accordance with certain embodiments presented herein.
Figure 15:
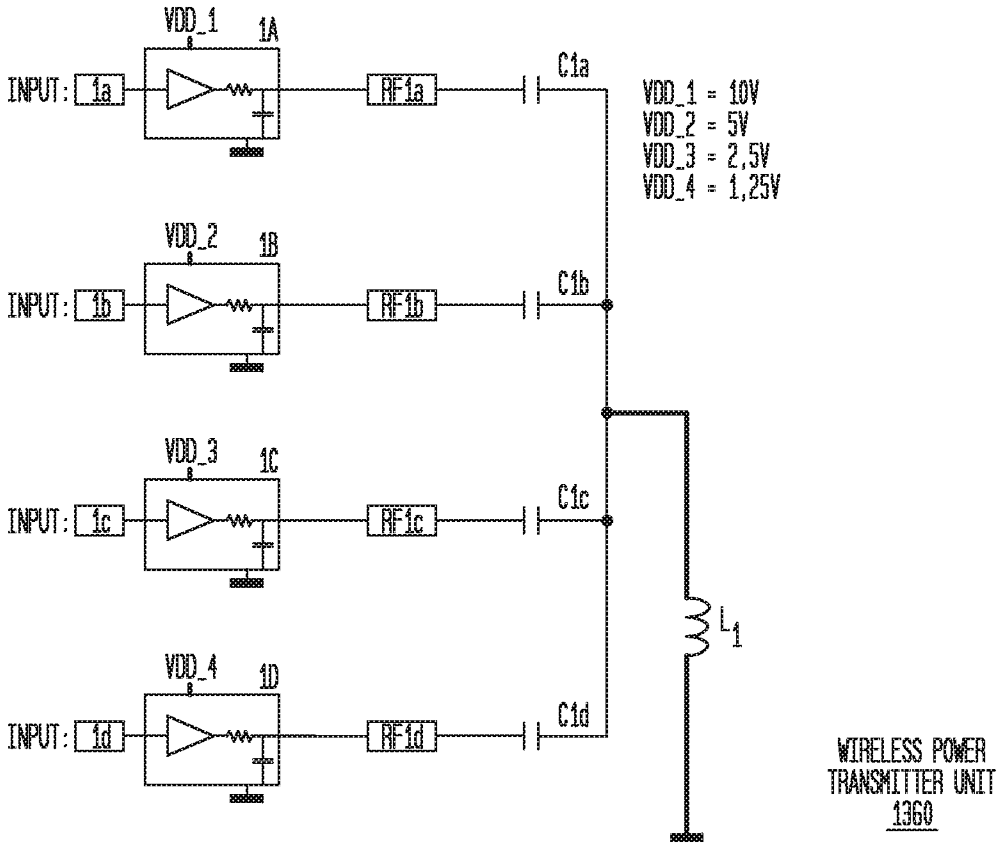
FIG. 15 is a schematic diagram illustrating a plurality of Class-D drivers forming a Class-H amplifier, in accordance with certain embodiments presented herein.

Embodiments have primarily been described above with reference to the use of Class-D amplifiers. However, as noted elsewhere herein, it is to be appreciated that the techniques presented herein can implemented with different amplifiers or bridges, such as Class-E, Class-F, Class-G or Class-H amplifiers. FIG. 14 is a schematic diagram illustrating a wireless power transmitter unit 1260 comprising a plurality of Class-E amplifiers, in accordance with certain embodiments presented herein. FIG. 15 is a schematic diagram illustrating a wireless power transmitter unit 1360 comprising a plurality of Class-D drivers each supplied with a different rail voltage forming a Class-H amplifier, in accordance with certain embodiments presented herein.

Figure 16:
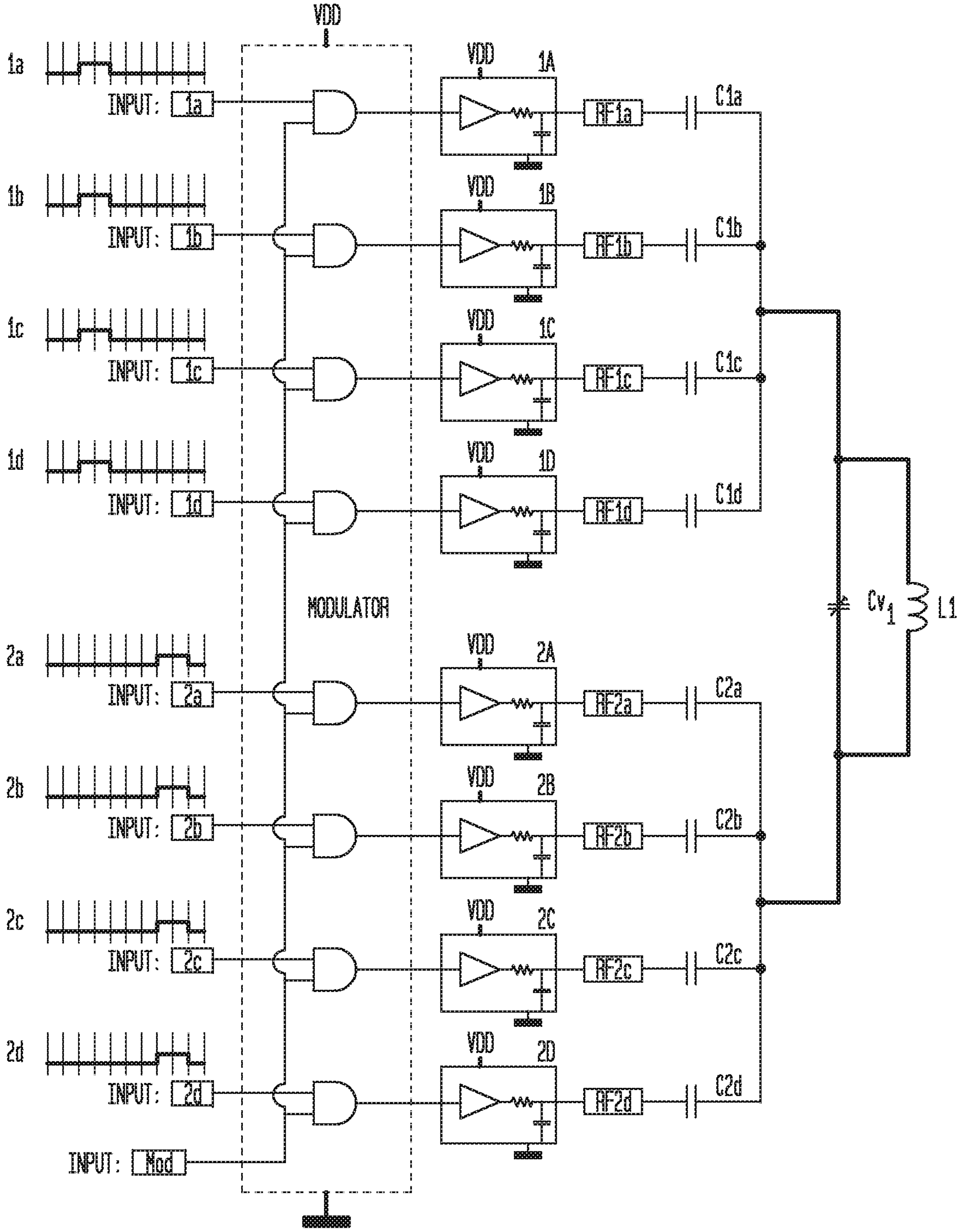
FIG. 16 is a schematic diagram illustrating a plurality of Class-D amplifiers with a data modulator, in accordance with certain embodiments presented herein.

FIG. 16 is a schematic diagram illustrating a plurality of Class-D amplifiers generating a quantized wave RF carrier that is modulated using OOK (On-Off keying) modulation scheme by means of a data modulator block, in accordance with certain embodiments presented herein. The invention is not limited to OOK modulation of the quantized wave, but may include other modulation schemes for example BPSK, FSK, QAM and QPSK.

Figure 17:
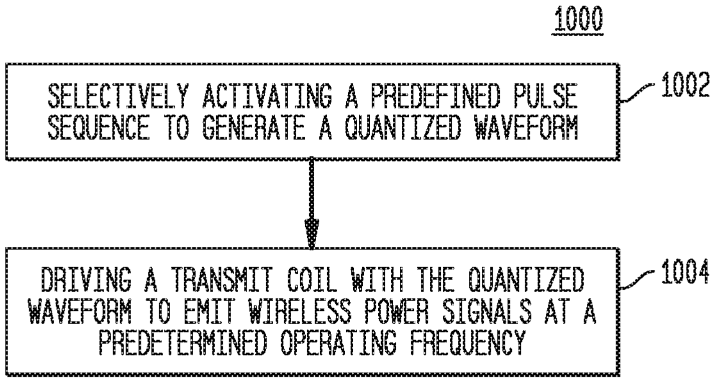
FIG. 17 is a flowchart of an example method, in accordance with certain embodiments presented herein.

FIG. 17 is a flowchart of a method 1000 in accordance with embodiments presented herein. Method 1000 begins at 1002 where a quantized waveform is generated by selectively activating a predefined pulse sequence. At 1004, a transmit coil is driven with the quantized waveform to emit wireless power signals at a predetermined operating frequency. This method allows to set or control the level of power transfer to the implant by adapting the predefined pulse sequences of the quantized waves shown in FIG. 4 and FIG. 6. In example the pulse sequence in FIG. 4A results in the lowest wireless power transfer and the pulse sequence shown FIG. 4N results in the highest wireless power transfer.

As noted elsewhere herein, the arrangements shown in FIGS. 3, 10, 12 and 14 are merely illustrative and that techniques presented herein may be implemented with different arrangements (e.g., different numbers of amplifiers, different groups of amplifiers, different numbers of capacitors, etc.). Also as noted elsewhere herein, embodiments presented herein have been primarily described with reference to an example auditory prosthesis system, namely a cochlear implant system. However, as noted above, it is to be appreciated that the techniques presented herein may be implemented by a variety of other types of implantable medical devices (or systems that include other types of implantable medical devices) and/or can be used to transfer power from a number of different inductive power transmission or charging devices (e.g., an inductive transfer primary) to a number of inductive power receiving devices (e.g., an inductive transfer secondary).

For example, the techniques presented herein may be implemented by other auditory prostheses, such as acoustic hearing aids, middle ear auditory prostheses, bone conduction devices, direct acoustic stimulators, electro-acoustic prostheses, other electrically simulating auditory prostheses (e.g., auditory brain stimulators), etc. The techniques presented herein may also be implemented by tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc. The techniques presented herein can also be used to provide power to (wirelessly charge), for example: wearable or portable electronic devices, such as smart watches, headphones, mobile phones, etc.; computing devices, such laptop computers, tablet computers, game consoles, etc.; Radio-frequency identification (RFID) tags, consumer electronic devices, such as power tools, electric toothbrushes, etc., appliances, etc.

Figure 18:
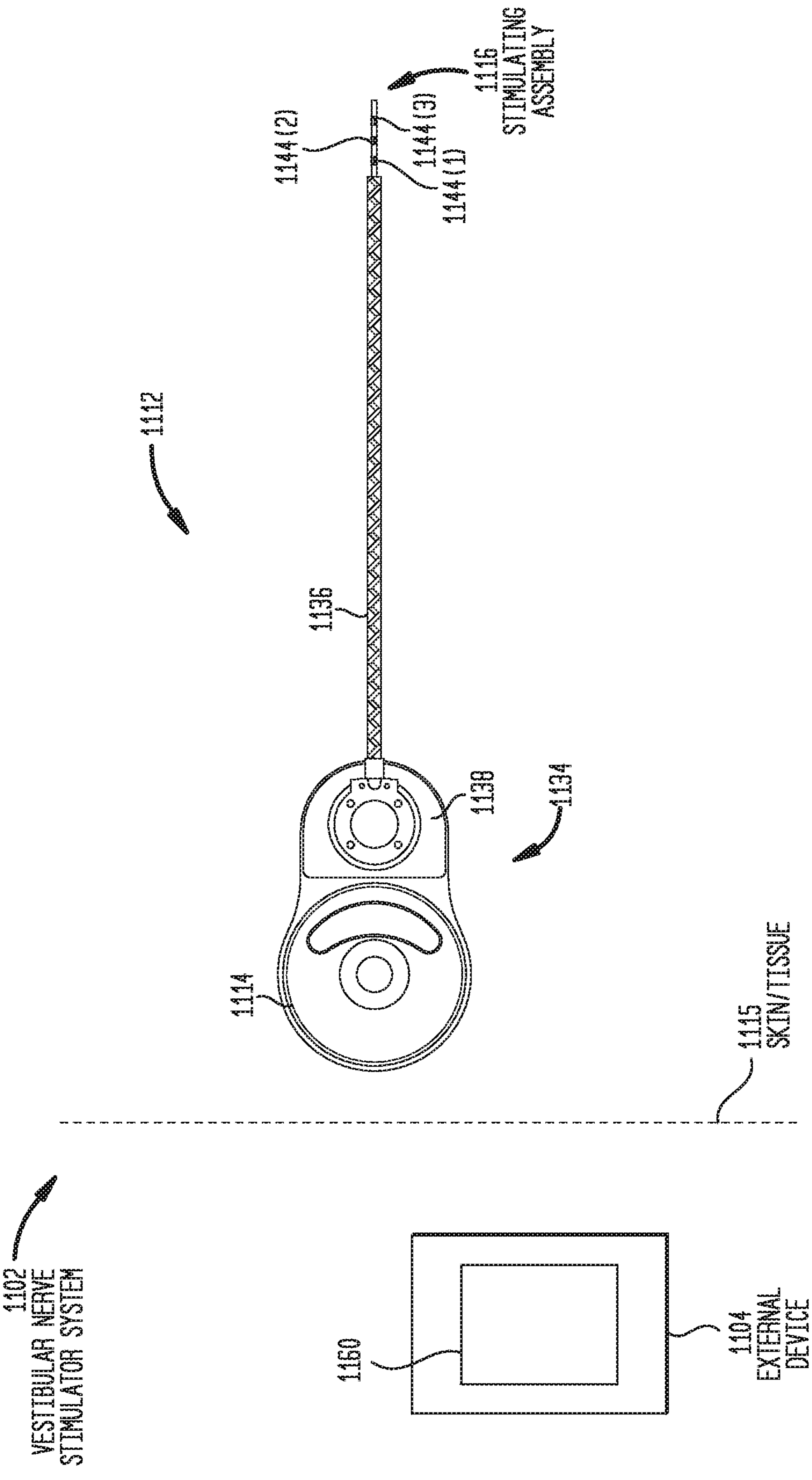
FIG. 18 illustrates an example vestibular stimulator system, in accordance with certain embodiments presented herein.

FIG. 18 illustrates an example vestibular stimulator system 1102, with which embodiments presented herein can be implemented. As shown, the vestibular stimulator system 1102 comprises an implantable component (vestibular stimulator) 1112 and an external device/component 1104 (e.g., external processing device, battery charger, remote control, etc.). The external device 1104 comprises a wireless power transmitter unit 1160 that may have an arrangement that is similar to, for example, wireless power transmitter units 360 or 860, described above. As such, the external device 1104 is configured to transfer power (and potentially data) to the vestibular stimulator 1112, The vestibular stimulator 1112 comprises an implant body (main module) 1134, a lead region 1136, and a stimulating assembly 1116, all configured to be implanted under the skin/tissue (tissue) 1115 of the recipient. The implant body 1134 generally comprises a hermetically-sealed housing 1138 in which RF interface circuitry, one or more rechargeable batteries, one or more processors, and a stimulator unit are disposed. The implant body 134 also includes an internal/implantable coil 1114 that is generally external to the housing 1138, but which is connected to the transceiver via a hermetic feedthrough (not shown).

The stimulating assembly 1116 comprises a plurality of electrodes 1144 disposed in a carrier member (e.g., a flexible silicone body). In this specific example, the stimulating assembly 1116 comprises three (3) stimulation electrodes, referred to as stimulation electrodes 1144(1), 1144(2), and 1144(3). The stimulation electrodes 1144(1), 1144(2), and 1144(3) function as an electrical interface for delivery of electrical stimulation signals to the recipient's vestibular system.

The stimulating assembly 1116 is configured such that a surgeon can implant the stimulating assembly adjacent the recipient's otolith organs via, for example, the recipient's oval window. It is to be appreciated that this specific embodiment with three stimulation electrodes is merely illustrative and that the techniques presented herein may be used with stimulating assemblies having different numbers of stimulation electrodes, stimulating assemblies having different lengths, etc.

It is to be appreciated that the embodiments presented herein are not mutually exclusive and that the various embodiments may be combined with another in any of a number of different manners.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A wireless power transmitter unit, comprising: a resonant tank circuit; and a quantized waveform generator having a single-ended output coupled to a first end of the resonant tank circuit, wherein the quantized waveform generator is configured to generate a predetermined quantized waveform that, when delivered to the resonant tank circuit, causes the resonant tank circuit to emit wireless power signals having a selected harmonic emission spectrum in which one or more predetermined harmonic emissions are substantially eliminated.

2. The wireless power transmitter unit of claim 1, wherein the quantized waveform generator comprises:

a plurality of amplifiers; and a pulse generator configured to independently drive each of the plurality of amplifiers with a plurality of pulse sequences that collectively generate a quantized waveform at an output of the plurality of amplifiers.

3. The wireless power transmitter unit of claim 1, wherein the resonant tank circuit comprises a radio-frequency (RF) coil and a plurality of distributed capacitors each connected in series with the RF coil.

4. The wireless power transmitter unit of claim 1, wherein the predetermined quantized waveform is a biphasic signal.

5. The wireless power transmitter unit of claim 2, wherein the plurality of pulse sequences include pulses that are shifted in time relative to one another.

6. The wireless power transmitter unit of claim 1, wherein the predetermined quantized waveform has an approximate sinusoidal shape.

7. The wireless power transmitter unit of claim 1, further comprising:

a data modulator configured to modulate the wireless power signals with data.

8. A wireless power transmitter unit, comprising: a transmit coil and a plurality of capacitors each connected in series with the transmit coil to form a resonant tank circuit; a quantized waveform generator comprising a plurality of amplifiers and a pulse generator configured to independently drive each of the plurality of amplifiers with a plurality of pulse sequences that generate to generate a quantized waveform, wherein the quantized waveform is input at the resonant tank circuit and induces to collectively induce an inductive power transmission at the resonant tank circuit from which one or more harmonic emissions are absent, having a selected harmonic emission spectrum in which one or more predetermined harmonic emissions are substantially eliminated, wherein the quantized waveform is delivered to only one end of the resonant tank circuit at given time while the other end of the resonant tank circuit is grounded.

9. The wireless power transmitter unit of claim 8, wherein each amplifier is coupled to the transmit coil by at least one of the plurality of capacitors.

10. The wireless power transmitter unit of claim 9, wherein a capacitance of each of the plurality of capacitors is equal.

11. The wireless power transmitter unit of claim 9, wherein a capacitance of each of the plurality of capacitors is binary scaled.

12. The wireless power transmitter unit of claim 9, wherein each one of the plurality of amplifiers is coupled to the transmit coil by a different one of the plurality of capacitors.

13. The wireless power transmitter unit of claim 8, wherein the plurality of capacitors are part of a capacitor array bank.

14. The wireless power transmitter unit of claim 8, wherein a first subset of the plurality of capacitors are part of a first capacitor array bank connected to a first node of the transmit coil, and a second subset of the plurality of capacitors are part of a second capacitor array bank connected to a second node of the transmit coil.

15. The wireless power transmitter unit of claim 8, wherein the plurality of capacitors and the transmit coil are matched to a predetermined tuning frequency.

16. A method, comprising: in a wireless power transmitter unit comprising a resonant tank circuit and a quantized waveform generator having a single-ended output coupled to a first end of the resonant tank circuit: generating, with the quantized waveform generator, a predetermined quantized waveform that, when delivered to the resonant tank circuit, causes the resonant tank circuit to emit wireless power signals having a selected harmonic emission spectrum in which one or more predetermined harmonic emissions are substantially eliminated.

17. The method of claim 16, wherein the quantized waveform generator comprises a pulse generator and a set of amplifiers that are grouped over a distributed resonance capacitor part of a series resonant tank circuit, and wherein the method comprises:

selectively driving a plurality of amplifiers in the set of amplifiers in a predefined sequence in order to generate a step function output comprising the predetermined quantized waveform.

18. The method of claim 17, wherein the predefined sequence used to drive the plurality of amplifiers is such that, when the predetermined quantized waveform is used to drive a transmit coil of the series resonant tank circuit, one or more harmonic components of a predetermined operating frequency are substantially eliminated.

19. The method of claim 18, wherein generating the predetermined quantized waveform comprises:

driving at least a first amplifier connected to the transmit coil with a first pulse sequence to create a first output waveform at a first node of the transmit coil; and driving at least one or more other amplifiers connected to the transmit coil with one or more other pulse sequences to create one or more other output waveforms at the first node of the transmit coil, wherein the first output waveform and the one or more other output waveforms are summed at the first node of the transmit coil to create the predetermined quantized waveform having multiple discrete levels at the first node of the transmit coil.

20. The method of claim 19, wherein the first output waveform and the one or more other output waveforms have a predetermined duty cycle such that, when summed at the first node of the transmit coil, one or more harmonic emissions of the predetermined operating frequency are eliminated.

21. The method of claim 19, wherein generating the predetermined quantized waveform comprises:

selectively driving the at least first amplifier and the at least one or more other amplifiers with a first pulse sequence and one or more other pulse sequences, respectively, each having a predetermined duty cycle that collectively create multiple output levels at the transmit coil.

22. The method of claim 16, further comprising:

modulating the wireless power signals with data.

* * * * *